US012631690B2

(12) United States Patent
Dawoud et al.

(10) Patent No.: US 12,631,690 B2
(45) Date of Patent: *May 19, 2026

(54) METHOD AND DEVICE FOR DETECTING ABNORMAL BATTERY CONSUMPTION DUE TO EXTRA-BATTERY MECHANISMS

(71) Applicant: Pacesetter, Inc., Sylmar, CA (US)

(72) Inventors: Fady Dawoud, Studio City, CA (US); Aditya Goil, Stevenson Ranch, CA (US); Kevin J. Davis, Thousand Oaks, CA (US)

(73) Assignee: Pacesetter, Inc., Sylmar (CA)

( * ) Notice: Subject to any disclaimer, the term of this patent is extended or adjusted under 35 U.S.C. 154(b) by 223 days.

This patent is subject to a terminal disclaimer.

(21) Appl. No.: 18/526,022

(22) Filed: Dec. 1, 2023

(65) Prior Publication Data

US 2024/0094304 A1 Mar. 21, 2024

Related U.S. Application Data

(63) Continuation of application No. 17/712,440, filed on Apr. 4, 2022, now Pat. No. 11,874,334.

(51) Int. Cl.
| | |
|---|---|
| *G01R 31/392* | (2019.01) |
| *G01R 31/367* | (2019.01) |
| *G01R 31/3835* | (2019.01) |
| *A61N 1/378* | (2006.01) |

(52) U.S. Cl.
CPC ......... *G01R 31/392* (2019.01); *G01R 31/367* (2019.01); *G01R 31/3835* (2019.01); *A61N 1/378* (2013.01)

(58) Field of Classification Search
None
See application file for complete search history.

(56) References Cited

U.S. PATENT DOCUMENTS

| | | | |
|---|---|---|---|
| 5,439,483 A | 8/1995 | Duong-Van | |
| 11,874,334 B2 * | 1/2024 | Dawoud | G01R 31/3835 |
| 2004/0015104 A1 * | 1/2004 | Goldberger | A61N 7/00 607/2 |
| 2006/0079938 A1 | 4/2006 | Fleenor et al. | |
| 2009/0246515 A1 | 10/2009 | Negi et al. | |

(Continued)

*Primary Examiner* — Jas A Sanghera
(74) *Attorney, Agent, or Firm* — Dean D. Small; Carroll, Hoette & Butscher, LLC

(57) ABSTRACT

Systems, methods, and devices are provided for determining an early battery depletion (EBD) condition of an implantable medical device that includes a memory storing program instructions and a processor executing the program instructions. Circuitry is electrically coupled to the processor, and the circuitry and processor perform one or more tasks related to at least one of collecting signals indictive of physiologic activity, analyzing collected signals, delivering therapy, or communicating with an external device. A battery supplies energy to the circuitry and processor. A monitoring circuit coupled to the battery measures actual energy usage from the battery representing at least one of a current draw from the battery during corresponding tasks or a voltage measurement across the battery. Circuitry and processor calculate projected energy usage from the battery in connection with the corresponding tasks, and determine when an EBD condition exists based on projected energy usage and actual energy usage.

20 Claims, 12 Drawing Sheets

(56)  References Cited

U.S. PATENT DOCUMENTS

| | | | |
|---|---|---|---|
| 2011/0098765 A1 | 4/2011 | Patel | |
| 2011/0245888 A1 | 10/2011 | Badelt et al. | |
| 2012/0316813 A1* | 12/2012 | Langheim | H01M 10/486 |
| | | | 702/63 |
| 2013/0289646 A1 | 10/2013 | Libbus et al. | |
| 2016/0000350 A1 | 1/2016 | Zhang | |

* cited by examiner

| Current Detection Scenario | Scope-Limiting Conditions | Rule Conditions |
|---|---|---|
| 1 | uses 2 current measurements, pt1, pt0, where pt0 is the latest<br><br>all points are measured after the '*PDA_Last_Session_timestamp*' | for each point, measured ave current(pt)><br>projected current(pt) *1.80 + 50 |
| 2 | uses 3 current measurements, pt2, pt1 pt0, where pt0 is the latest<br><br>all points are measured after the '*PDA_Last_Session_timestamp*' | for each point, measured ave current(pt)><br>projected current(pt) *1.50 + 50 |
| 3 | uses 4 current measurements, pt3, pt2, pt1, pt0, where pt0 is the latest<br><br>all points are measured after the '*PDA_Last_Session_timestamp*' | for each point, measured ave current(pt)><br>projected current(pt) *1.20 + 40 |
| 4 | uses 5 current measurements, pt4, pt3, pt2, pt1, pt0, where pt0 is the latest<br><br>all points are measured after the '*PDA_Last_Session_timestamp*' | for each point, measured ave current(pt)><br>projected current(pt) *1.20 + 30 |
| 5 | uses 6 current measurements, pt5, pt4, pt3, pt2, pt1, pt0, where pt0 is the latest<br><br>all points are measured after the '*PDA_Last_Session_timestamp*' | for each point, measured ave current(pt)><br>projected current(pt) *1.20 + 20 |

FIG. 5

| Voltage Detection Scenario | Scope-Limiting Conditions | Rule Conditions |
|---|---|---|
| 1 | uses 3 BV measurements, pt2, pt1, pt0, where pt0 is the latest<br>latest point is not in relaxation<br>latest point value < ref V<br>latest point is not postponed measurement<br>latest point is newer than telemetry | voltage drop > predetermined V<br>comparisons of BV and PBV < predetermined V |
| 2 | uses 3 BV measurements, pt2, pt1, pt0, where pt0 is the latest<br>latest point is in relaxation<br>latest point value< ref V<br>latest point is not postponed measurement<br>latest point is measured after telemetry | voltage drop > predetermined V<br>comparisons of BV and PBV < predetermined V |
| 3 | uses 4 BV measurements, pt3, pt2, pt1, pt0, where pt0 is the latest<br>latest 2 points have value < ref V<br>High battery usage (HBU) event occurred for pt0 > 1 day<br>pt2, pt1, pt0 are not postponed measurements<br>all points are measured after telemetry | two voltage drops > predetermined first V and/or second V<br>comparisons of<br>BV and PBV < predetermined V |

FIG. 7A

| | | |
|---|---|---|
| 4 | uses 5 BV measurements, pt4, pt3, pt2, pt1, pt0, where pt0 is the latest<br>latest 3 points have value < ref V<br>all points are measured after telemetry<br>HBU event occurred for pt0 > 5 days ago<br>pt3, pt2, pt1, pt0 are not postponed measurements | three voltage drops > predetermined first V, second V and/or third V<br>comparisons of<br>BV and PBV < predetermined V |
| 5 | uses 5 BV measurements, pt4, pt3, pt2, pt1, pt0, where pt0 is the latest<br>latest 3 points have value < ref V<br>all points are measured after telemetry<br>HBU event for pt0 >= 4 days ago and HBU event for pt0 <= 6 days ago<br>pt3, pt2, pt1, pt0 are not postponed measurements | three voltage drops > predetermined first V, second V and/or third V<br>comparisons of<br>BV and PBV < predetermined V |
| 6 | uses 2 BV measurements, pt1, pt0, where pt0 is the latest<br>latest point is NOT in relaxation<br>both points have value < ref V<br>both PBV (points) values are > ERI (172*0.01504)<br>latest point are measured after telemetry<br>HBU event for pt0 = 1 day old<br>both points are not postponed | both points < PBV + PBV margin |

FIG. 7B

METHOD AND DEVICE FOR DETECTING ABNORMAL BATTERY CONSUMPTION DUE TO EXTRA-BATTERY MECHANISMS

REFERENCE TO RELATED APPLICATIONS

The present application is a continuation application of, and claims priority to, U.S. application Ser. No. 17/712,440, filed on 4 Apr. 2022, the complete subject matter of which is expressly incorporated herein by reference in its entirety.

BACKGROUND

Embodiments of the present disclosure generally relate to methods and devices to detect early battery depletion (EBD) conditions in a battery powered device that are related to extra-battery mechanisms.

A variety of implantable medical devices (IMDs) and portable external electronic medical devices (EMDs) are utilized today in connection with a wide array of health-related topics. Some implantable and external portable medical devices utilize various types of battery-based power supplies, which ultimately need to be replaced or recharged. Although the timing for replacement of the battery can be tracked in order to avoid loss of power by the medical device, some devices may sustain failure mechanisms from outside of the battery that can drain the battery, and thus the battery can reach an end of service condition earlier than expected. Battery failure may have various negative implications, such as in pacemaker dependent patients, in patients utilizing cardiac resynchronization devices and in patients utilizing an implantable defibrillator.

Heretofore, processes have been proposed to monitor battery usage and to track/predict a remaining life of the battery or to predict an EBD condition. For example, a method has been proposed to determine a charge consumption drawn externally from a battery cell by the device for a select period of time. The method obtains a measured cell voltage for the battery cell and calculates a projected cell voltage based on the charge consumption and usage conditions. The method declares an EBD condition based on a relation between the measured and projected cell voltages.

However, the foregoing and other solutions only account for certain aspects of a condition/life of an IMD/EMD. The foregoing and other solutions have not addressed mechanisms outside of the battery that can drain the battery. By way of example, one mechanism that can occur outside the battery (e.g., extra-battery) is hermeticity seal breach that occurs when the moisture seal is breached, allowing bodily fluids to leak through. This can manifest as current shorts between exposed electrical components that drain the battery. Other mechanisms that drain the battery are faulty electrical circuit component(s) outside the battery that cause short circuit(s) and/or firmware code that can lead to incessant operation and high current drain. These conditions can shorten the overall life of the battery and thus the IMD/EMD.

A need remains for methods and devices that monitor the conditions that can lead to an EBD condition that can shorten the expected lifespan of the battery in the IMD/EMD.

SUMMARY

In accordance with embodiments herein a system comprises an implantable medical device (IMD). A memory is configured to store program instructions and a processor is configured to execute the program instructions. Circuitry is electrically coupled to the processor, and the circuitry and processor perform one or more tasks related to at least one of i) collecting signals indicative of physiologic activity, ii) analyzing the signals collected, iii) delivering a therapy, or iv) communicating with an external device. A battery supplies energy to the circuitry and the processor in connection with performing the one or more task. A monitoring circuit is coupled to the battery and measures an actual energy usage from the battery that represents at least one of a current draw from the battery during the corresponding tasks or a voltage measurement across the battery. The circuitry and processor also calculate a projected energy usage from the battery in connection with the corresponding tasks and determine when an early battery depletion (EBD) condition exists based on the projected energy usage and the actual energy usage.

Optionally, the EBD condition may be indicative of a failure condition that is unrelated to a battery state and the calculation of the projected energy usage from the battery in connection with the corresponding tasks can be based in part on programmed device parameters. The EBD condition can be indicative of a failure condition that is related to a failure in at least one of the circuitry, the processor, a lead, hermeticity seal break, or malfunctioning software or firmware.

Optionally, in connection with measuring the actual energy usage associated with a first task within the one or more tasks, the monitoring circuitry obtains current measurement values of current drawn from the battery while the circuitry and the processor perform the first task, and combine the current measurement values to obtain the actual energy usage associated with the first task. The monitoring circuitry may repeat the obtain and combine operations across multiple tasks within the one or more tasks.

Optionally, the actual energy usage includes a current drawn actually from the battery while performing a corresponding task, and the projected energy usage includes a projected current expected to be drawn from the battery while performing a corresponding task. In connection with measuring the actual energy usage, the voltage measurements across the battery may be a measured cell voltage at a point in time.

Optionally, the determination of the EBD condition may include identifying a current detection scenario that compares the actual energy usage to the projected energy usage and evaluating a collection of scope-limiting conditions related to the current detection scenario. The projected energy usage may be combined with a tolerance, and the EBD condition may be identified when the actual energy usage is greater than the projected energy usage with the tolerance. The collection of scope-limiting conditions may include evaluating a predetermined number of points within an interrogation period that are uninterrupted in time by a telemetry session.

Optionally, the determination of the EBD condition includes identifying a voltage detection scenario that compares a plurality of the voltage measurements within an interrogation period and evaluating a collection of scope-limiting conditions related to the voltage detection scenario. The collection of scope-limiting conditions may include at least one of i) determining whether at least one of the voltage measurements is in relaxation, ii) determining whether at least one of the voltage measurements is greater than a predetermined voltage value, iii) determining whether at least one of the voltage measurements is a postponed measurement, or iv) determining whether at least one of the voltage measurements is newer than a most recent telemetry session, and wherein the determination of the EBD condition further includes evaluating a collection of rule conditions that include at least one of i) determining one or more voltage drop of the voltage measurements that exceeds predetermined limits, or ii) at least one of the voltage measurements is below a projected voltage level combined with a safety margin.

Optionally, the determination of the EBD condition may include identifying a first detection scenario that compares the actual energy usage to the projected energy usage. The first detection scenario may be a current detection scenario or a voltage detection scenario and includes a collection of scope-limiting conditions. In response to satisfying the collection of scope-limiting conditions, a collection of rule conditions related to the first detection scenario may be evaluated, and in response to the collection of rule conditions indicating that the EBD condition is not occurring, a second detection scenario may be identified to determine the EBD condition.

In accordance with embodiments herein, a method, under control of one or more processors, is configured with specific executable instructions to use a battery to supply energy to circuitry and the one or more processors in connection with performing tasks related to at least one of i) collecting signals indicative of physiologic activity, ii) analyzing the signals collected, iii) delivering a therapy, or iv) communicating with an external device. The method directs a monitoring circuit to measure an actual energy usage from the battery. The actual energy usage represents at least one of a current draw from the battery during the corresponding tasks or a voltage measurement across the battery. The method calculates a projected energy usage from the battery in connection with the corresponding tasks, and determines when an EBD condition exists based on the projected energy usage and the actual energy usage.

Optionally, the method receives programmed device parameters and stores the programmed device parameters in a memory. The method determines the EBD condition based on the actual energy usage occurring after the programmed device parameters are received, wherein calculating the projected energy usage from the battery in connection with the corresponding tasks is based in part on the programmed device parameters. The programmed device parameters may include at least one of pacing current usage by various leads attached to the device, pacing rate, pacing pulse width, pacing pulse shape, pacing voltage, or percent chamber pacing.

Optionally, the EBD condition may be indicative of a failure condition that is related to a failure in at least one of the circuitry, the processor, a lead, hermiticity seal break, or malfunctioning software or firmware.

Optionally, the determination of the EBD condition may include identifying a current detection scenario that compares the actual energy usage to the projected energy usage and evaluating a collection of scope-limiting conditions related to the current detection scenario.

Optionally, the projected energy usage may be further calculated based on measured pacing lead impedances.

Optionally, the determination of the EBD condition may include identifying a voltage detection scenario that compares a plurality of the voltage measurements within an interrogation period and evaluating a collection of scope-limiting conditions related to the voltage detection scenario.

BRIEF DESCRIPTION OF THE DRAWINGS

FIG. 5 illustrates a plurality of current detection scenarios in accordance with embodiments herein.

FIGS. 7A and 7B illustrate a plurality of voltage detection scenarios in accordance with embodiments herein.

DETAILED DESCRIPTION

Figures 1A, 1B:
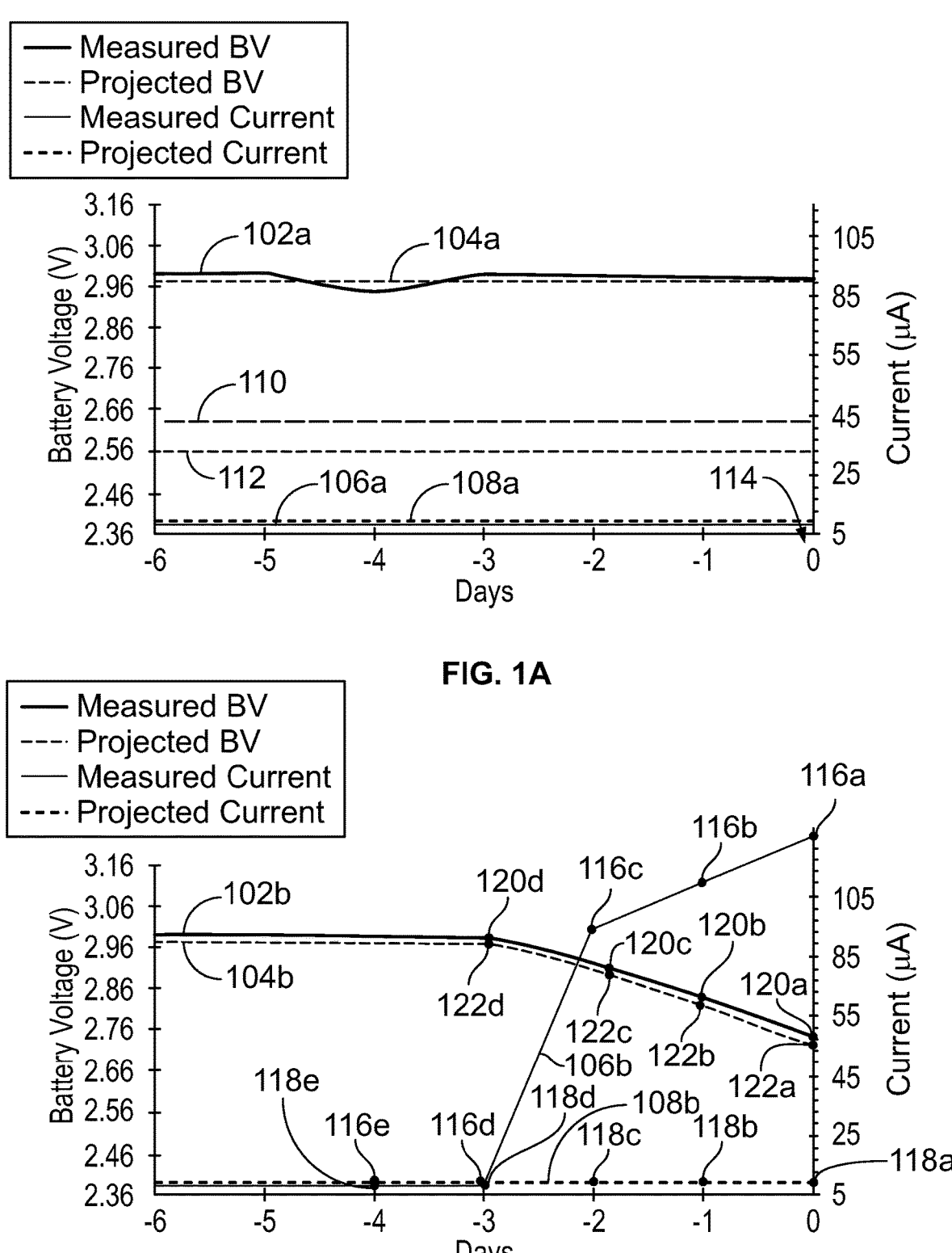
FIGS. 1A-1D illustrate voltage and current curves of an IMD indicative of a normal device condition and several abnormal device conditions that can indicate an early battery depletion condition failure in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Definitions

The term "task" refers to predefined operations to be performed by a medical device over a useful life of the medical device. The predefined operations may be in connection with delivering therapy, pacing, monitoring and/or collecting signals (e.g., signals indicative of physiologic activity), communicating with other devices, self-diagnostics, internal maintenance, and the like. Nonlimiting examples of device related tasks include reforming capacitors, delivering shocks or other therapy, performing telemetry operations, transmitting and receiving RF communications, performing expected self-discharge (about 1% per year) and the like.

The terms "projected cell voltage", and "projected battery voltage", "PV", and "PV$_{EST}$" as used herein, refer to a voltage that may be derived from a predetermined model, formula or other pre-existing information. For example, projected cell voltages are indicated in a model shown in FIG. 2A in connection with various amounts of capacity that are consumed from a model battery cell.

The term "projected battery voltage margin", as used herein, refers to the projected battery voltage (e.g., projected BV) that has been shifted by a constant safety margin.

The terms "early battery depletion condition", "early battery depletion", and "EBD condition", as used herein, refer to the battery being depleted in advance of the expected battery lifespan, such as by reaching an elective replacement indicator voltage level or an end of service voltage level earlier than expected. An EBD condition can be detected in advance of reaching the elective replacement indicator voltage level by using the methods and systems described herein.

The term "measured average current", as used herein, refers to the average daily current measured by the device as consumed by all or a portion of the extra-battery mechanisms.

The term "projected current" as used in connection with describing operation of the medical device, refers to a total implantable medical device current usage that can be estimated by summation of the current usage by sub-components of each hardware circuitry, firmware circuitry, and software. The estimate is based on programmed device parameters and/or measurements associated with sub-components of the device. These sub-components can consist of background IMD functionality (including firmware, EGM signal sensing, accelerometer, etc.), telemetry current usage (including at least RF and Bluetooth communication, etc.), pacing current usage by various leads (including atrial, right ventricle, left ventricle (LV), and multi-point LV) taking into account pacing rate (beats-per-minute), pacing pulse width (msec), pacing pulse shape (e.g., decaying exponential), pacing voltage, percent chamber pacing, and lead impedance.

The term "projected current margin", as used in connection with describing operation of the medical device, is the projected current plus a fixed safety margin.

The term "high drain", as used in connection with describing various tasks performed by the medical device, refer to tasks that draw at least a predetermined amount of charge, current or voltage from the cell, over time or per unit time. For example, high drain or heavy current usage tasks may be itemized by task name or task type (e.g., a capacitor charging task, capacitor reforming task, high-power communications task, telemetry task, and the like). As another example, a high drain or heavy current usage task may represent a task that causes the battery cell to experience a transient voltage drop that does not fully recover for some period of time (e.g., a few days).

The terms "low drain" and "low current usage", as used in connection with describing operation of the medical device, refer to all operations that are not high drain or heavy current usage tasks. For example, low drain or low current usage operations may be itemized by task name or task type (e.g., pacing, providing power to the microprocessors, A/D conversion, recording cardiac signals in memory). As another example, a low drain or low current usage operation represents continuous operations, during which the battery cell does not experience transient voltage drops.

The terms "battery", "battery cell" and "cell" are used interchangeably to refer to a single cell as well as more than one cell connected in parallel or series to form a common power supply. The cell(s) may be rechargeable or primary cells that are designed to be used once and then discarded. Non-limiting examples of the types of cells include Lithium/Silver Vanadium Oxide, a combination lithium/silver vanadium oxide & carbon monofloride, and the like.

The term "extra-battery", as used in connection with describing various tasks performed by the medical device, refers to mechanisms that draw at least an amount of charge (e.g., current or voltage) from the cell, over time or per unit time. Mechanisms include anything outside the confines of the battery, such as leads that connect with a patient, software, firmware, processors, hardware, etc.

The terms "current detection scenario" and "voltage detection scenario" as used in connection with describing operation of the medical device, include a collection of scope-limiting conditions that define when the processor may evaluate the scenario and a collection of rule conditions that can indicate an EBD condition. The "current detection scenario" evaluates measured values and projected values of charge and/or current, while the "voltage detection scenario" evaluates measured values and projected values of voltage. The scenarios can compare measured and projected values to limits, ranges, and the like. The term "collection" as used herein can refer to one or more than one.

The term "scope-limiting condition", as used in connection with describing the current and voltage detection scenarios, includes one or more factors that limit when the scenario is evaluated, including but not limited to the measured voltage level of the battery, the relation of measured values in time to a telemetry session, and/or whether a relaxation flag, overshoot flag, and/or postponed flag is True or False.

The term "rule condition", as used in connection with describing the current and voltage detection scenarios, includes rules that compare measured and projected values to indicate an early battery depletion condition.

The terms "relaxation" and "relaxation flag", as used in connection with describing operation of the medical device, indicate a qualifying ON/OFF daily flag that is set by the device using rules to determine when high battery usage has occurred (e.g., high drain) and to indicate that battery measurements are during a period of ongoing relaxation. Relaxation is required for the battery voltage to recover after high current usage, and the voltage measurements during relaxation are expected to be lower than typical measurements outside of relaxation.

The terms "overshoot" and "overshoot flag", as used in connection with describing operation of the medical device, indicate a qualifying ON/OFF daily flag that is set by the device using rules to state that measurement during this period might have a battery voltage measurement higher than the actual voltage measurement, and that the battery measurement should be expected to have possibly higher voltage values than when not in overshoot.

The terms "postponed" and "postponed flag", as used in connection with describing operation of the medical device, indicate a TRUE/FALSE flag. TRUE indicates that the battery voltage measurement was skipped for the day because of reasons configured into the device operation, which include overlapping timers, high priority activities, and timeout conditions that can indicate whether a daily battery voltage measurement was postponed.

The term "telemetry flag", as used in connection with describing operation of the medical device, indicates a TRUE/FALSE flag. TRUE indicates that a telemetry session has occurred on that day.

The term "elective replacement indicator" (ERI), as used herein, can indicate that when the battery voltage level reaches the predetermined ERI voltage level, replacement of the medical device may be considered.

The term "end of service" (EOS), as used herein, can indicate a battery voltage level wherein the medical device may not be fully operational.

The following variables, as used throughout the present application, shall have the following means:

$I_{ss}(t)$=Steady state current drawn externally from a battery cell by a device such as when performing low drain or low current usage operations. The steady state current draw may be measured in real-time during operation of the device or may be represent a set or programmed value that is predetermined from tests, calculations or otherwise.

$I_{char}$=Current drawn externally from a battery cell by the device for a high drain charging task to charge a shock therapy storage circuit (e.g., capacitor). The current draw may be measured in real-time during operation of the device or may be represent a set or programmed value that is predetermined from tests, calculations or otherwise.

$I_{tele}$=Current drawn externally from a battery cell by the device during a high drain telemetry/communications task. The current draw may be measured in real-time during operation of the device or may be represent a set or programmed value that is predetermined from tests, calculations or otherwise.

$T_{char}$=time spent performing the high drain charging task (e.g., charging capacitors or other shock therapy storage circuits).

$T_{tele}$=time spent performing the high drain telemetry/communications task.

$C_{ss}(n)=$ $$\int_{t=0}^{T_n} I_{ss}(t)dt$$

=Total steady state charge consumption from a starting point to a set point in time (n). The total steady state charge consumption is obtained by integrating current from steady state power usage $I_{ss}(t)$, such as for pacing and running the computer and A/D conversion.

$C_{tele}(n)=I_{tele}*T_{tele}$ (n)=Telemetry related charge consumption obtained by multiplying the average current draw during a telemetry task times the time spent performing telemetry.

$C_{char}(n)=I_{char}*T_{char}$ (n)=Charging related charge consumption obtained by multiplying the average current draw during a charging task times the time spent performing charging.

$C_{task}$ $(n)=I_{task}*T_{task}(n)$=Total task related charge consumption for all tasks that are tracked by the medical device. The total task related charge consumption is obtained by multiplying the corresponding average current draw during a task times the time spent performing the task, and summing the task related charge consumption for all tasks that are tracked. The total task related charge consumption includes the projected telemetry related charge consumption, charging related charge consumption and all other task related charge consumption (other than steady state charge consumption).

$C_{tot}(n)=C_{SS}(n)+C_{tele}(n)+C_{char}(n)+C_{task}(n)=$Total charge consumption drawn externally from the battery cell by the device from a set starting point up to a point in time (n) from all charge demands BV (n)=Cell voltage measured at a point in time "n". The cell voltage may be measured periodically (e.g., each day) utilizing a voltage measurement circuit with (within) the medical device.

BVest(n)=Projected cell voltage that is determined utilizing a capacity v. voltage model (e.g., a lookup table), where the projected cell voltage is based on the total charge consumption $C_{tot}(n)$.

Normal and Abnormal Battery Consumption Trends

FIGS. 1A-1D illustrate voltage and current curves of an IMD indicative of a normal device condition and several abnormal device conditions that can indicate an early battery depletion (EBD) condition in accordance with embodiments herein. The left vertical axis plots battery voltage in volts and the right vertical axis plots current in microamps. The horizontal axis plots time in days that shows an interrogation period from day 0 to day −6.

FIG. 1A shows normal battery voltage and current trends over a 7-day period. FIG. 1A illustrates a solid line corresponding to measured battery voltage (BV) 102a and a dashed line corresponding to a projected BV 104A, which may also be referred to a projected cell voltage. Similarly, a solid line corresponding to measured average current 106a and a dashed line corresponding to a projected current 108a are shown. The measured BV 102a and projected BV 104a at least partially overlap and the measured average current 106a and projected current 108a at least partially overlap, although there could be larger deviations between the measured and projected indicators while the associated device remains in normal operation.

Over time and normal operation, the measured voltage drops to a certain level and can reach an elective replacement indicator (ERI) 110 (shown with a dashed line). If maintained in service, the measured voltage can ultimately reach an end of life or end of service (EOS) 112 (shown with a dashed line), such as in about 6 months for a pacemaker and 3 months for an implantable cardioverter defibrillator. It is recognized that the voltages, currents, and voltage levels of the ERI 110 and EOS 112 illustrated in FIG. 1A are examples and are not limiting.

In some embodiments an external device, one or more processors within the implantable device, and the like can interrogate the measured and projected indicators, which may have been measured, collected, and/or calculated and stored in a memory. In FIGS. 1A-1D, an interrogation period or window can be a 7-day period over which data associated with the measured and projected voltage and current can be analyzed and compared. The interrogation period can also be shorter or longer than 7-days. Referring to FIG. 1A, a device interrogation 114 can be accomplished at day 0, wherein day 0 is the day of interrogation and the curves associated with the measured BV 102, projected BV 104, measured average current 106, and projected current 108 extend from day 0 to 6 days prior (e.g., day −6). By way of example, extended RF telemetry use may result in a transient change in the measured BV 102a at day −4, but not in the projected BV 104a.

FIG. 1B shows a deviation of the measured average current 106b from the projected current 108b over the interrogation period from day 0 through day −6. One or more processors can activate one or more modules, such as an early depletion (ED) detector and detection scenario module, that compare at least some of the measured and projected voltage and current data based on scenarios, rule conditions, scope-limiting conditions, and the like as discussed further below. Different scenarios can have different scope-limiting conditions and thus some, all, or none of the rule conditions will be evaluated during a given interrogation period.

For example, if the scope-limiting conditions of a scenario are met, the one or more processors can compare data points from within the interrogation period. A data point (pt) can correspond with each of the days, wherein pt0 corresponds to day 0, pt1 corresponds to day −1, pt2 corresponds to day −2, and so on. Referring to the measured average current 106b, measured average current pts 116a, 116b, 116c, 116d, 116e correspond to pt0, pt1, pt2, pt3, and pt4, respectively. Projected current pts 118a, 118b, 118c, 118d, 118e are shown on the projected current 108b. Not all of the pts on the voltage and current curves are shown in FIG. 1B. Because the measured average current 106a and the projected current 108b substantially overlap over a portion of the graph as displayed, single dots are used to indicate the two pts 116d and 118d and the two pts 116e and 118e. The processors can compare the measured average current pts 116 and the corresponding projected current pts 118 according to rule conditions within the applicable current detection scenarios to determine if an EBD condition is present. Based on the unexpected deviation of the measured average current 106b from the projected current 108b over at least a portion of the data points within the interrogation period, the processor can identify that an EBD condition is present. In some embodiments the one or more current detection scenarios may identify the EBD condition at day −1 within the interrogation window.

Turning to the voltage curves, the voltage levels of both the measured BV 102b and the projected BV 104b decline. Measured BV pts 120a, 120b, 120c, 120d and projected BV pts 122a, 122b, 122c, 122d are shown. The processors can compare the pts 120 and 122 according to rule conditions within applicable voltage detection scenarios to determine if an EBD condition is present. In some cases, even though the battery voltage may decline unexpectedly prior to the expected ERI 110 (FIG. 1A), an EBD condition may not be detected by analyzing voltage measurements alone as the measured BV 102b and projected BV 104b track each other as expected.

Figure 1C:
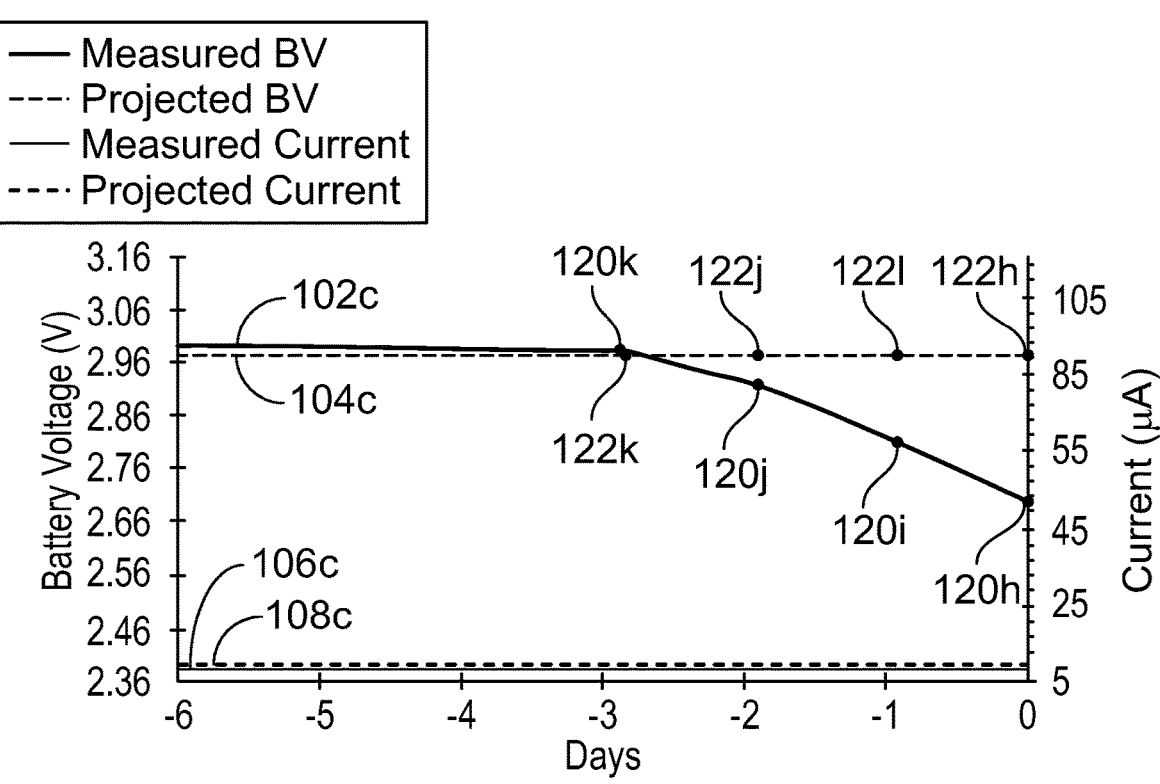

FIG. 1C shows a drop in the measured BV 102c in comparison with the projected BV 104c over the interrogation period (e.g., 7-day period). The processors can compare pts (not shown) along the measured average current 106c and the projected current 108c according to rule conditions within applicable current detection scenarios. As the measured average current 106c and projected current 108c track each other, and the projected current 108c is slightly greater than the measured average current 106c, no EBD condition is identified based on the current values. The processors can also compare pts 120h, 120i, 120j, 120k along the measured BV 102c and pts 122h, 122i, 122j, 122k along the projected BV 104c according to rule conditions within applicable voltage detection scenarios to determine if an EBD condition is present. In some embodiments, the EBD condition may be identified at day −1 (e.g., an unexpected drop in the measured BV 102c) based on one or more of the voltage detection scenarios.

Figure 1D:
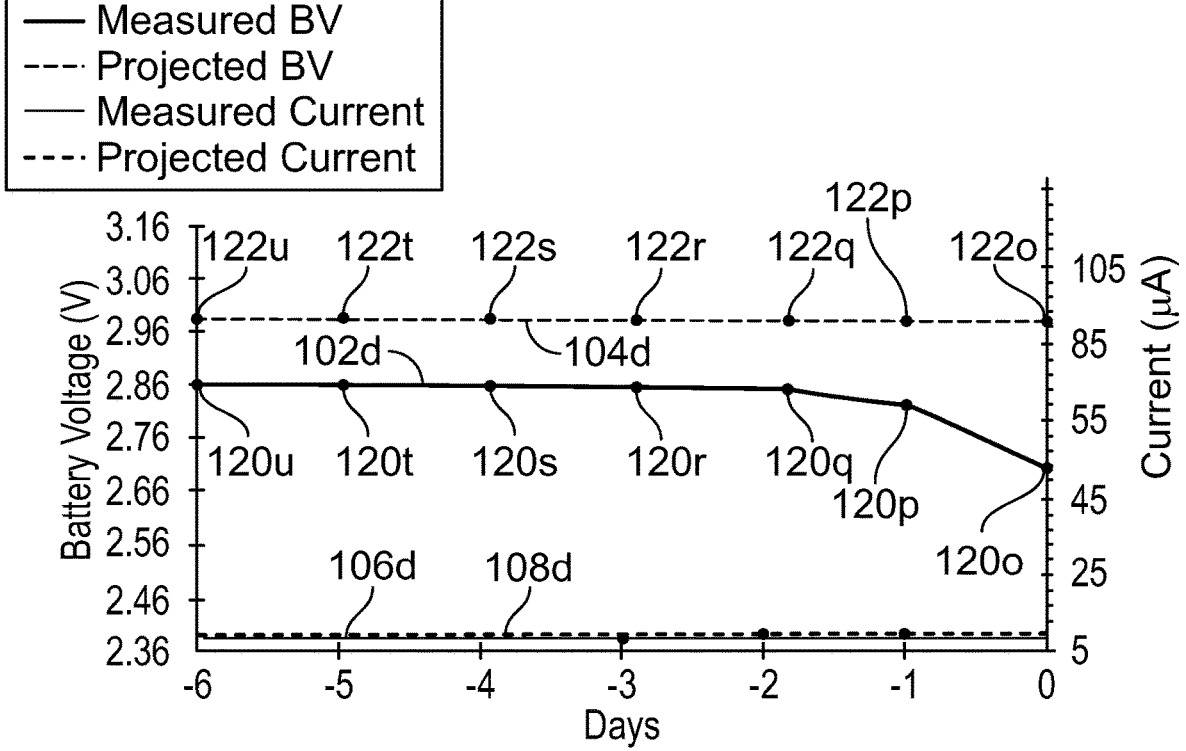

FIG. 1D shows a measured BV 102d that has deviated below the projected BV 104d over the interrogation period. Similar to FIG. 1C, the measured average current 106d and the projected current 108c track each other as expected and thus no EBD condition is identified based on the applicable current detection scenarios. The processors can compare two or more pts 120o, 120p, 120q, 120r, 120s, 120t, 120u along the measured BV 102d and pts 122o, 122p, 122q, 122r, 122s, 122t, 120u along the projected BV 104d according to rule conditions within applicable voltage detection scenarios to determine if an EBD condition is present. In some embodiments, the EBD condition may be identified at day −5 based on the voltage different between compared pts as determined by one or more of the voltage detection scenarios.

A technical advantage of the systems and methods herein includes the analysis of measured and projected voltage, current, and/or charge levels over time to determine whether the device battery is experiencing an EBD condition (e.g., premature battery depletion). Programmed device settings and measurements of sub-components can be applied to achieve accurate estimated values compared to general estimates based on baseline values or device norms. The analysis can be accomplished by executing a series of rules that can detect abnormalities under various conditions. The analysis of data such as session records, snapshots of device memory and/or log files can be accomplished locally within a patient's IMD, by a device such as a smartphone, or a remote care network, such as the Merlin.net patient care network.

In accordance with embodiments herein, methods and systems are described for detecting abnormal or unexpected voltage drops and/or decreases and transient and/or maintained current drains that result from faulty extra-battery components. The methods and systems implement various techniques to declare abnormal battery depletion by extra-battery mechanisms. The methods and systems also provide one or more indicators to inform the patient, and/or health care professionals of an EBD condition and a potential impeding battery failure. Non-limiting examples of warning indicators include vibration and/or sounds emitted by a medical device. Other non-limiting examples include transmitting warnings wirelessly (e.g., Bluetooth, WiFi) to another electronic device, such as a patient's personal digital devices (e.g., cell phones, tablet device, laptop computer, etc.), a bedside monitoring device and the like. The receiving device may then convey a visual and/or audible indication to the patient and/or health care professional.

In accordance with embodiments herein, the methods and systems for detecting abnormal battery consumption by extra-battery mechanism may be implemented on one or more external devices operating alone or in combination with a portable battery-powered medical device. For example, the methods described herein may be implemented in hardware and/or software loaded on an external device such as the Merlin@Home™ device or a similar device. The method can compare measured battery performance against a predicted performance saved on the external device, where data space is less limited as compared to memory capacity of implantable medical devices.

Determination of Charge Consumption and Measured BV

Figure 2A:
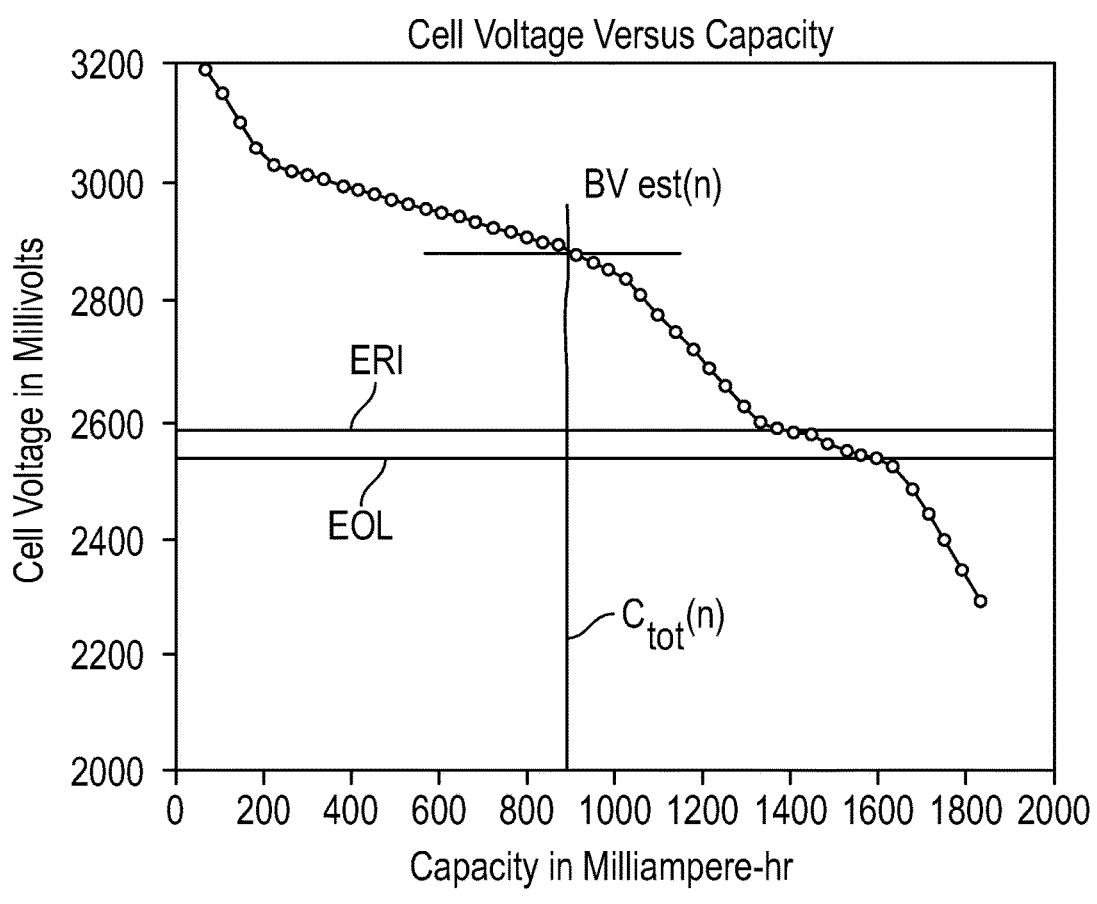
FIG. 2A exhibits a predictable cell voltage versus capacity profile for a model battery cell, such as a high-quality cell made with chemically pure, predictable constituents in accordance with embodiments herein.

FIG. 2A exhibits a predictable cell voltage versus capacity profile for a model battery cell, such as a high-quality cell made with chemically pure, predictable constituents. The horizontal axis plots battery capacity expended/discharged in milliamps hours, while the vertical axis plots the cell voltage. The curve in FIG. 2A shows that when the voltage drops to a certain level, the cell has reached the elective replacement indicator (ERI) and ultimately will reach the end of life (EOL) (e.g., EOS), such as in about 6 months for a pacemaker and 3 months for an implantable cardioverter defibrillator. Optionally, voltage measurements may be obtained to determine a cell voltage by connecting a standard load to the battery cell (e.g., a 100 K ohm load; or a load that draws a fixed current; e.g., 30 μA). Once the standard load is applied, a voltage potential across the load can be measured. It is recognized that the voltages or shape of the curve illustrated in FIG. 2A is an example and is not limiting. The voltage-capacity curve is calibrated for average daily background current usage.

In the example of FIG. 2A, at the beginning of the battery life (e.g., fully charged, when no capacity has been expended), the battery exhibits an initial voltage of approximately 3200 mV (3.2 V). After being utilized for a period of time, during which the battery expends approximately 200 mA-hours of the initial full charge, the battery voltage drops to about 3 V, where the battery voltage is maintained over a substantial majority of the remaining capacity of the battery until approaching the end-of-life condition. Prior to reaching an end-of-life condition, the battery voltage begins to drop at an increasing rate (e.g., when the battery has expended approximately 875 mA-hours of the batteries capacity) until reaching a point at which the battery cell has expended about 850 mA-hours (designated as the early replacement indicator (ERI)). Once the battery voltage reaches the ERI, the battery voltage drops relatively quickly over a relatively small amount of the overall battery capacity (e.g., dropping 300 mV over the discharge of approximately 200 mA-hours). The battery voltage ultimately drops below the EOL voltage (e.g., when approximately 1800 mA-hours of capacity have been utilized). The ERI indicator designates that the battery is sufficiently depleted to warrant battery replacement. In some devices, the ERI indicator may designate that the entire device should be replaced, which may involve explant of an implantable medical device or otherwise. It is recognized that the curve in FIG. 2A is merely one example.

However, simply determining that the cell voltage has dropped to some specified threshold level may not be effective in detecting self-discharge of a cell. As explained herein, methods and systems are provided to monitor a state of discharge of a battery cell and/or a rate of battery depletion in order to detect impending early battery failure before it happens. For instance, if a pacemaker circuit draws 10 microamperes from a battery having a capacity of 100 microampere-years and delivers 10 microamperes for 9 years, then 90 microampere-years has been consumed and about 10 percent of the 100 microampere-years capacity remains.

The charge usage may be determined in various manners. As an example, battery use can be monitored by continuously integrating a current drawn from the battery. Continuous monitoring may be achieved utilizing a current monitoring circuit and/or a current monitoring device (e.g., a coulometer) to measure the state of discharge. Current monitoring devices, such as a coulometer, can measure the current externally drawn from the battery.

Voltage may be used to monitor the state of discharge of high-rate batteries when the current drain is more or less constant. However, when the battery experiences high current use, such as during capacitor reforming or delivering shocks, or high-power communication, the battery exhibits a transient voltage drop followed by a transient recovery interval that ends with a slight overshoot in voltage. In some embodiments, the battery voltage may not be used to monitor the state of charge during a transient recovery interval. After a predetermined period of time (e.g., several days to a few weeks), the voltage returns to a steady state level that accurately reflects the state of battery charge.

Figure 2B:
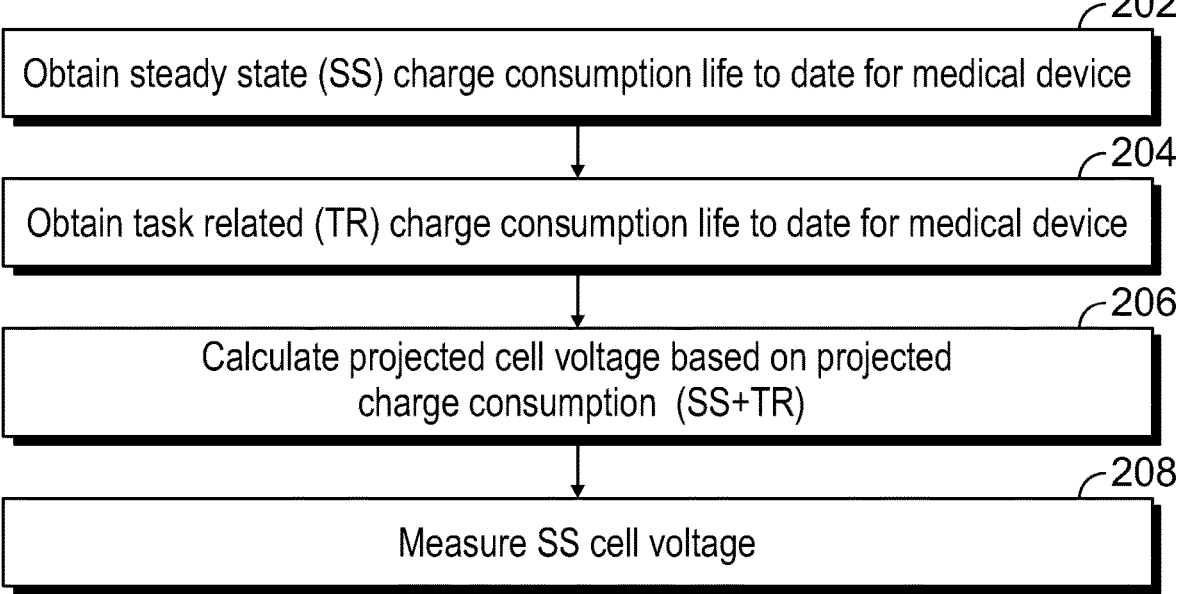
FIG. 2B illustrates a method for determining charge consumption and a projected battery voltage in accordance with embodiments herein.

FIG. 2B illustrates a method for determining charge consumption and a projected BV in accordance with embodiments herein. In some embodiments, the charge consumption can be used to determine a projected BV and a measured average current. The operations in the method of FIG. 2 may be implemented in whole or in part by a portable medical device carried by a patient, an IMD, an external device, a remote server, a workstation or a combination thereof.

At 202, one or more processors of the medical device obtain a steady state consumption $C_{ss}$ that is externally drawn from a battery cell and consumed by the medical device over some select period of time, during which the medical device experiences a steady state demand. For example, the steady state consumption $C_{ss}$ may be a value saved in memory of the medical device that is continuously or periodically updated (independent of any other operations in FIG. 2B). As another example, the processor may maintain a SS timer that tracks an amount of time that the medical device has operated in a steady state since the battery cell was fully charged. The processor may multiply the value of the SS timer by a steady state current draw $I_{ss}(t)$. Optionally, the processor may integrate estimated and/or measured steady state current/charge consumption over the select period of time.

At 204, the one or more processors of the medical device monitor and/or estimate a task related charge that is externally drawn from a battery cell and consumed by the medical device over the select period of time, during which the medical device performs one or more tasks. For example, the task related charge consumption may be a value saved in memory of the medical device that is continuously or periodically updated (independent of any other operations of FIG. 2B). As another example, the processor may maintain task related timers for each type of task (e.g., a charging task timer $T_{char}$, telemetry task timer $T_{tele}$). The timers are multiplied by the corresponding current draw and then summed to obtain the total projected task related charge consumption. As another example, the processor may integrate (in real-time) estimated and/or measured task-related current/charge consumption $C_{task}$ attributable to any and all device related tasks.

The estimated and/or measured steady state and task related consumption at 202 and 204 are combined to determine a total charge consumption $C_{TOT}$ externally drawn from the battery cell by the medical device. During normal operation, the total charge consumption externally drawn from the battery cell by the medical device would equal the total charge consumption of the battery cell. In accordance with embodiments herein, the operations at 202 and 204 may directly measure the steady state and task related consumption. By way of example, each medical device may include a measurement circuit that is configured to directly measure the current/charge consumed during some period of time, such as the steady state demand and/or during certain tasks (e.g., high drain tasks, low drain tasks). For example, a charge monitoring circuit (e.g., hardware-measured charge consumption) may be provided with (or within) the medical device. The charge monitoring circuit directly measures the rate at which current/charge is consumed over each task to directly measure and integrate the total current/charge consumed in connection with the task. Charge consumption is converted into measured average current for the device, such as, for example, on a daily basis (e.g., to calculate a daily change) or over a predetermined time period.

Additionally or alternatively, in accordance with embodiments herein, the operations at 202 and 204 may utilize estimates for the steady state and task related consumption, where the estimates are based on a set of predetermined baseline consumption levels. For example, baseline consumption levels may be assigned to steady state demand and each task, where the baseline consumption level is derived from theoretical calculations. Additionally or alternatively, baseline consumption levels may be derived from tests performed using one or more "baseline" medical devices. For example, a baseline medical device may be directed to perform a task (e.g., capacitor reforming task), during which test equipment measures the current and/or charge that is consumed. The measured average current/charge drain is integrated over a duration of the task to obtain a total current/charge that is consumed by the medical device during the task. The test may be repeated by the medical device multiple times and/or may be performed by multiple medical devices, in order to obtain an average baseline consumption level associated with the corresponding task. One or more baseline medical devices may be directed to perform multiple different types of tasks (e.g., telemetry, pacing, etc.) to derive a set of predetermined baseline consumption levels for corresponding tasks.

Thereafter, any and/or all medical devices that are manufactured to the same or similar specification as the baseline medical device(s) (e.g., with the same battery, shocking capacitors, etc.) may be assigned all or a portion of the set of predetermined baseline consumption levels. When an implanted medical device performs a capacitor reforming task, the baseline consumption level for capacitor reforming may be recorded as the amount of current/charge that is consumed, without directly measuring the current/charge consumed. Similarly, each time the medical device performs a capacitor charging task or communications task, the associated baseline consumption level is obtained from memory and recorded as the amount consumed.

Additionally or alternatively, the operations at 202 and 204 may estimate a rate at which current is consumed during tasks and during steady state conditions. The estimated rate may be utilized as a baseline rate of current/charge consumption. Thereafter, when a medical device performs certain tasks or maintains certain conditions (e.g., capacitor reforming task, maintains a steady state operation), the duration of the task/condition is measured and combined (e.g., multiply) with the baseline rate of current/charge consumption to determine the total charge consumption from the battery cell of the device during the select period of time.

The foregoing calculation or measurement may be performed in connection with additional tasks, such as delivering therapy, monitoring signals, communicating with other devices, self-diagnostics, internal maintenance, and the like. The foregoing calculation and/or measurement may be performed in connection with delivering shocks or other therapy, performing telemetry operations, transmitting and receiving RF communications, performing projected self-discharge and the like. The calculation and measurements provide a set of baseline consumption levels for predetermined tasks.

At 206, the one or more processors determine a projected cell voltage $BV_{est}$ based on the total charge consumption $C_{tot}$ (steady state and/or task related charge) externally drawn from the battery. For example, the processors may reference a cell voltage versus capacity model, such as the curve illustrated in FIG. 2A. As one example, when the charge consumption by the medical device equals 400 mA-hours, at 206, the processors may determine that the projected cell voltage should be approximately 3000 mV. As another example, when the charge consumption (steady state and task related charge) totals approximately 900 mA-hours, the projected cell voltage would be slightly more than 2850 mV.

Accordingly, the projected cell voltage BVest can be estimated based on the method of FIG. 2B utilizing a cell voltage vs. capacity model (e.g., lookup curve in FIG. 2A) and the total charge consumption $C_{tot}$ determined at 202 and 204. The process described in connection with FIG. 2B can also estimate a projected cell voltage BVest(n) for a select point in time based on a total charge consumption $C_{tot}(n)$ that is tracked over time.

At 208, the medical device measures a voltage across the battery cell, such as with a voltage measuring circuit. For example, the voltage may be measured at the terminals of the cell, such as to avoid downstream components within the medical device from affecting the measurement. When the medical device utilizes a feedthrough at an interface between the cell and electronic components within the medical device, the voltage may be measured at battery terminals extending through the feedthrough. Alternatively, when voltage effects of downstream components are not of concern (or are of interest in the measurement), the voltage may be measured at a downstream location, such as at terminals provided on the housing of the medical device. Alternatively, the voltage may be measured at the input contacts of the switch network provided upstream of the terminals on the housing of the medical device. The measurement of voltage may be performed at other locations as well, when interference from other internal components of the medical device are not of concern.

By way of example, when voltage transients are present during a portion of a discharge operation, the processors may delay the measurement operation in order that the cell voltage is measured after the voltage transients have settled. For example, the cell voltage may be measured after the voltage transients have settled down following high current demand conditions. As one example, the cell voltage may be measured after waiting a number of days following a high current demand condition. Additionally or alternatively, the processors may determine the point at which to measure the cell voltage based on a rate of change per unit time in the cell voltage. For example, the processors may monitor the rate of change per unit time (dV/dt) in the cell voltage and wait until the cell voltage dV/dt has settled to a predetermined level (e.g., a sufficiently low level following high current conditions). Once the rate of change per unit time in the cell voltage falls below the predetermined level, the cell voltage may then be considered to represent a steady-state level, in which case the measurement at 208 obtains a steady-state measured cell voltage.

Figure 3:
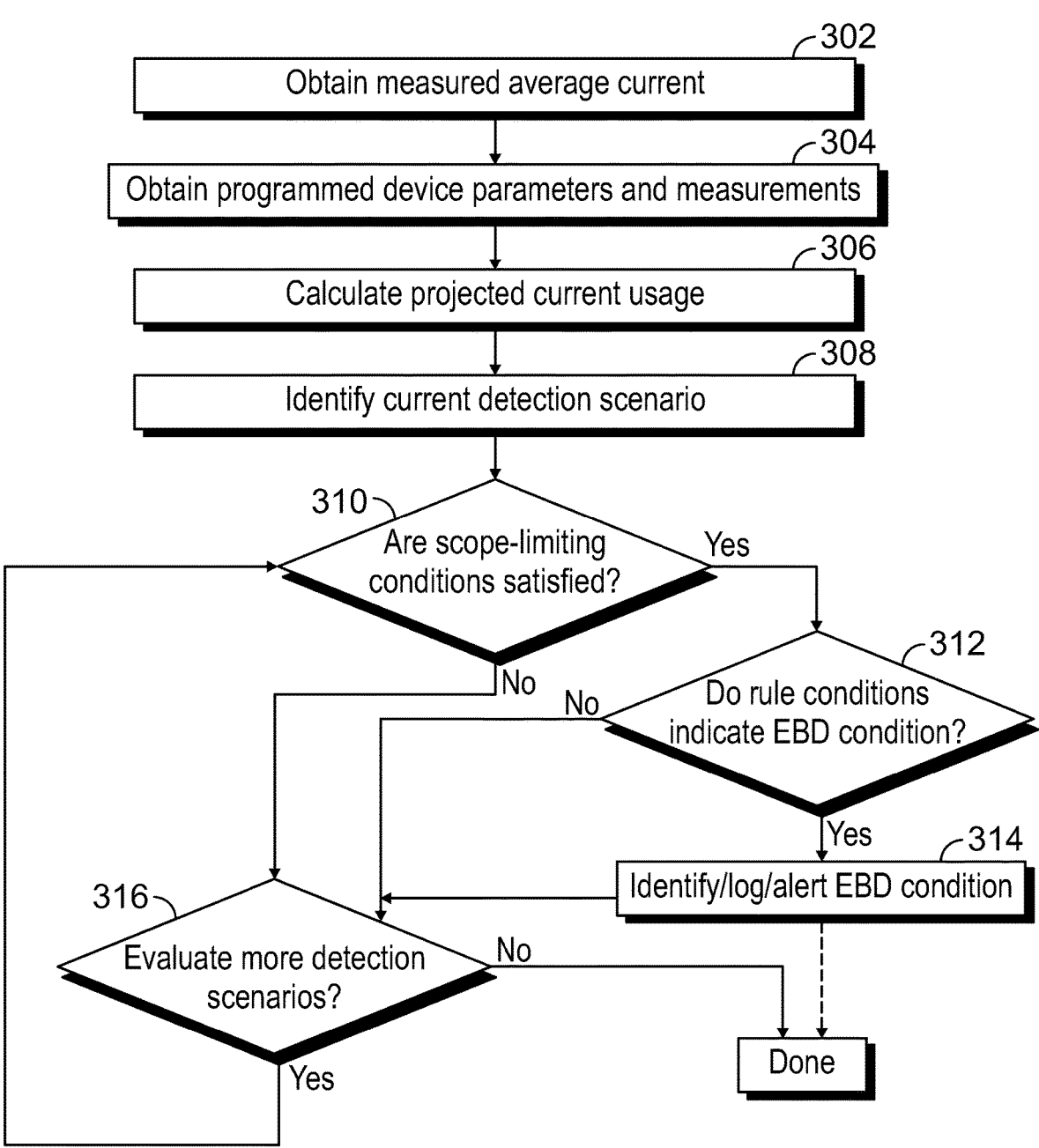
FIG. 3 illustrates a method for evaluating current detection scenarios associated with measured average current and projected current usage to identify EBD condition(s) in accordance with embodiments herein.

Projected Average Current Calculation Method and Identification of Current-Related EBD Condition FIG. 3 illustrates a method for evaluating current detection scenarios associated with the measured and projected currents to identify EBD condition(s) in accordance with embodiments herein. The operations of FIG. 3 may be implemented by hardware, firmware, circuitry and/or one or more processors housed partially and/or entirely within an IMD, a local external device, remote server or more generally within a healthcare system. Optionally, the operations of FIG. 3 may be partially implemented by an IMD and partially implemented by a local external device, remote server or more generally within a healthcare system. For example, the IMD includes IMD memory and one or more IMD processors, while each of the external devices/systems (e.g., local, remote or anywhere within the healthcare system) include external device memory and one or more external device processors.

Figure 4A:
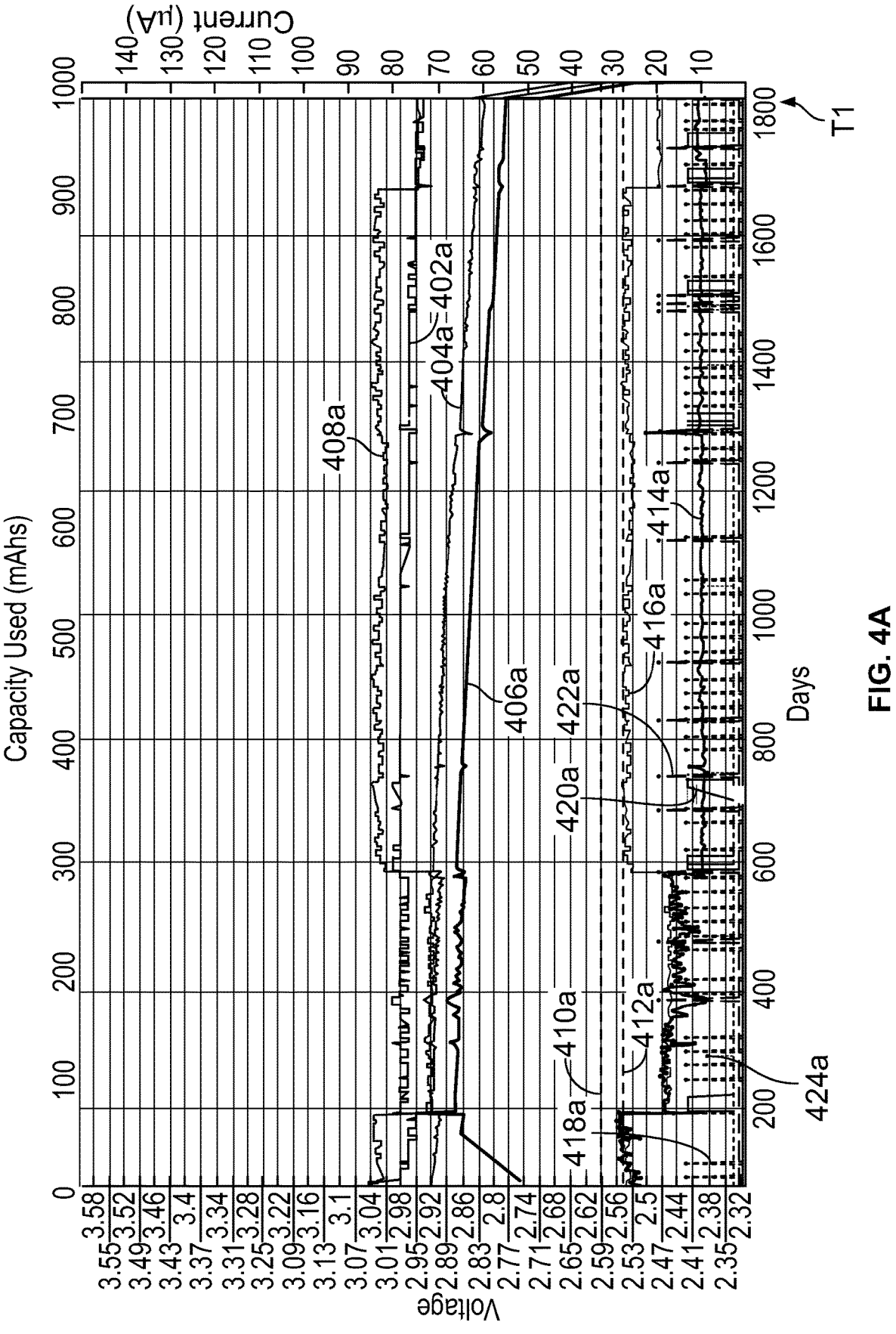
FIGS. 4A and 4B show examples of curves associated with abnormal battery behavior that can be caused by extra-battery mechanisms and result in an EBD condition in accordance with embodiments herein.
Figure 4B:
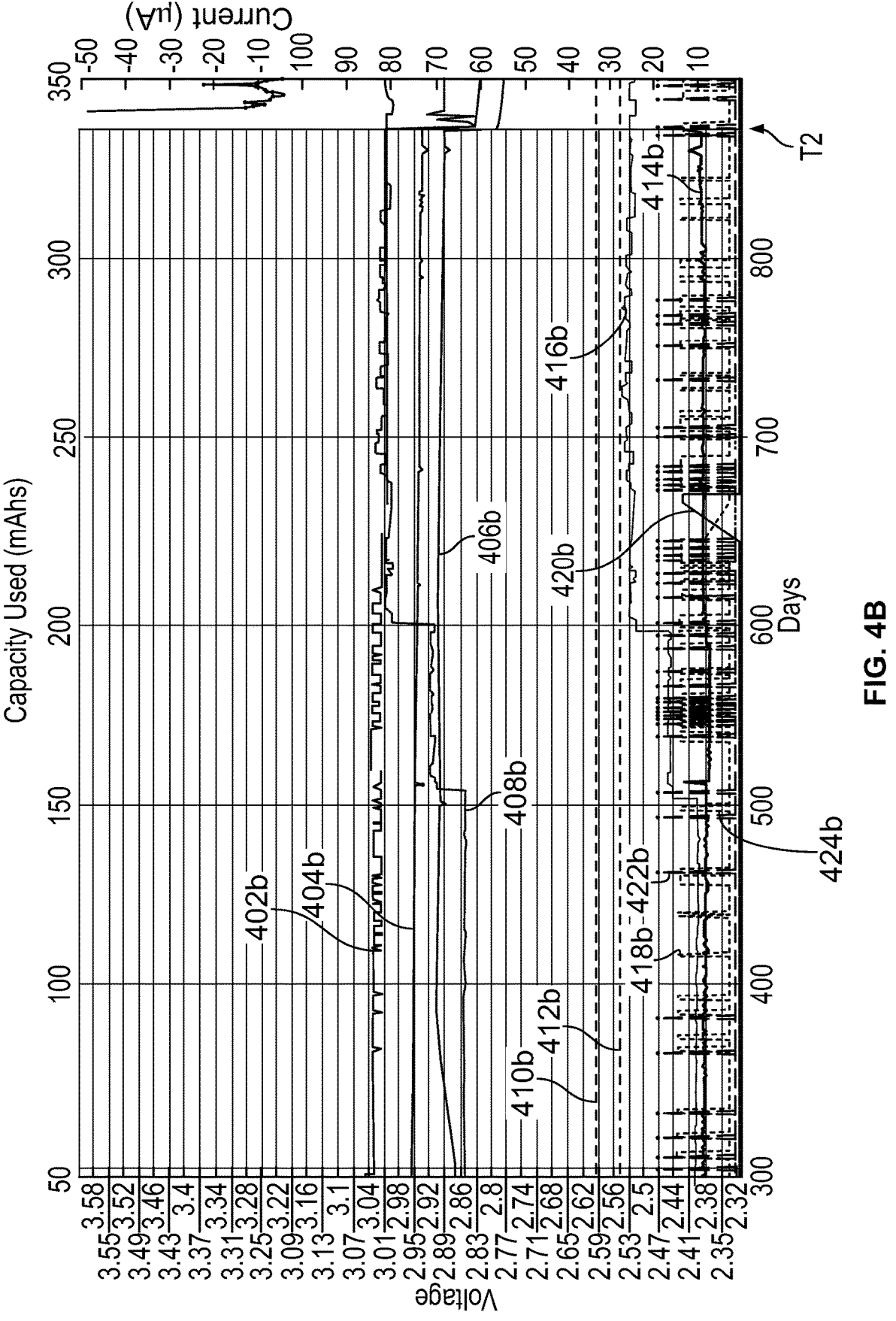

FIGS. 4A and 4B show examples of curves associated with abnormal battery behavior that can be caused by extra-battery mechanisms in accordance with embodiments herein. Among other things, the curves track charge consumption and voltage. The curves of FIG. 4A show both persistent deviation of the measured voltage from the projected voltage and an unexplained measured voltage drop, as well as a concurrently unexplained measured current deviation from projected current at T1. FIG. 4B shows an unexplained measured current deviation from projected current without persistent voltage abnormality at T2. The horizontal axis plots time in days along the bottom (not all days are individually shown) and capacity used in milliamp-hours along the top, while the left vertical axis plots battery voltage in volts and the right vertical axis plots current in microamps. The timeline can start from implantation of the IMD or at a later selected date.

Referring to both FIGS. 4A and 4B, these figures show measured BV 402a, 402b (e.g., BV measured at 208 of FIG. 2B), projected BV 404a, 404b, and projected BV margin 406a, 406b. The voltage levels for elective replacement (ERI) 410a, 410b and end of service (EOS) 412a, 412b are shown with dashed horizontal lines. Measured average current 414a, 414b, projected average current 416a, 416b, and projected current margin 408a, 408b are shown. Along the bottom of the graph, relaxation flags 418a, 418b, overshoot flags 420a, 420b, postponed flags 422a, 422b, and telemetry flags 424a, 424b are shown, which are flags/indicators used by one or more of the EBD condition algorithm(s) to determine whether data points should be used. FIGS. 3, 4A, and 4B will be discussed together.

At 302 of FIG. 3, one or more processors obtain measured average current, such as from over an interrogation period (e.g., on a weekly basis or other regular schedule, on-demand, based on a trigger, etc.) In some embodiments, the measured average current can be derived from the total charge consumption $C_{tot}(n)$ to provide an actual average current usage value for each day (or other identified time increment). In other embodiments, the actual average current usage value can be determined by measuring actual current drawn by extra-battery elements/circuits such as during a task (e.g., pacing), and calculating an average current over an amount of time that associated circuit(s) are operative. For example, a current monitoring circuit can measure an average current across a duration by obtaining current measurement values of current drawn from the battery while the circuitry and processor perform one or more tasks. A plurality of tasks can occur over the course of one day (e.g., 24-hour period) or other measurement period and in some cases, tasks can occur concurrently.

At 304, one or more processors obtain programmed device parameters and measurements, which will be used to calculate the projected current usage of sub-components and/or extra-battery components of the IMD (e.g., projected current 416). The programmed device parameters can include, for example, the pacing settings configured in a clinic setting and/or remotely by a caregiver. The programmed device parameters can also include background functionality, telemetry current usage, and the like. Measurement can include measured pacing lead impedances. For example, each pacing lead can have a lead impedance that can vary on a day-to-day basis and can be measured.

At 306, one or more processors calculate the projected current 416 based on the factors obtained and determined at 304. For example, the processors calculate the projected current 416 based on programmed pace pulse amplitudes and widths, pacing auto-capture settings, measurements of pacing lead impedances, etc. The projected current 416 can be calculated using, for example, values based on normal conditions wherein all of the device parameters are operating (e.g., pacing is active, etc.). The calculated projected current 416 is a spot-based current consumption, which is current consumed at a single point in time, and thus can be a single value representing a time period, such as one day. In some embodiments, the calculated projected current 416 can include a safety margin, fixed safety margin, tolerance, etc., that increases the value. For example, referring to FIG. 4A, at approximately day 1600 the value of the projected current 416a is approximately 30 microamps and the value of the measured average current 414a is approximately 12 microamps, while the projected current margin 408a is approximately 85 microamps.

At 308, one or more processors identify a current detection scenario to compare the actual energy usage, reflected in the measured average current 414, to the projected energy usage, reflected in the projected current 416. In some embodiments the projected current 416 can include the aforementioned tolerance.

At 310, one or more processors determine whether scope-limiting conditions of the current detection scenario are satisfied. For example, the processors can compare two or more points to detect one or more deviations between the measured average current 414 and the projected current 416 combined with a tolerance.

FIG. 5 illustrates a plurality of current detection scenarios in accordance with embodiments herein. It should be understood that other current detection scenarios can be used with the same, some, or different scope-limiting conditions and rule conditions. Referring to FIG. 4a, the processor can identify the telemetry flag 424a within an interrogation period. In some embodiments, such as in the scope-limiting conditions of FIG. 5, only points following the telemetry flag 424a would be considered. In some embodiments, the current detection scenario 1 can be used to detect an event of relatively higher severity that happens over a short amount of time (e.g., two days), while the current detection scenarios 2-5 detect events of relatively smaller severity that happen over relatively longer amounts of time (e.g., three-six days).

Referring to FIGS. 1B and 5, if telemetry flag 424 occurred at day −3 (not shown), only the measured average current points 116a, 116b, 116c may be considered, while if the telemetry flag 424 occurred at day −4, the measured average current pt 116d may also be considered. This process can identify if a predetermined number of consecutive points of the measured average current 106 are within the interrogation period and are measured after the last session wherein the IMD was interrogated by a remote device and/or conducted a telemetry session. This ensures that the programmed device parameters remain the same for all of the points used. For example, if telemetry flag 424 occurred at day −3, the processor determines that the scope-limiting conditions are satisfied for the current detection scenarios 1 and 2. However, the scope-limiting conditions are not satisfied for the current detection scenarios 3, 4, or 5.

Returning to FIG. 3, if all scope-limiting conditions of the current detection scenario are satisfied, flow moves to 312 where one or more processors determine whether rule conditions indicate an EBD condition. Referring again to FIGS. 1B and 5, and specifically at current detection scenario 1, the processors can determine if each of the measured average currents pts 116*a* and 116*b* at day 0 and day −1, respectively, are greater than a weighted projected current (e.g., (the projected current pt 118*a multiplier)+an additional set tolerance). If the rule conditions for each point are satisfied, the processors determine that an EBD condition is indicated. With respect to FIGS. 4A and 4B, an extreme increase in the measured average current 414*a* and 414*b* occurs around time T1 and T2, respectively. This increase in the measured average current 414 indicates a possible EBD condition.

If the processors determine that the rule conditions indicate an EBD condition, flow passes to 314 where the one or more processors identify and/or log the EBD condition that is indicative of a failure condition that is unrelated to a battery state. In some embodiments, the one or more processors can initiate a warning to notify the patient and/or health care professionals of an EBD condition. In some embodiments the warning can be a communication that is output or transmit to indicate that the device may experience an EBD state. The flow can either continue to 316 or be complete.

Returning to 312, if the rule conditions of the current detection scenario do not indicate an EBD condition, flow passes to 316 where one or more processors determine if there are more detection scenarios to evaluate. For example, if the processors just evaluated the current detection scenario 1, the flow may return to 310 and the one or more processors continue to evaluate current detection scenarios 2, 3, and so on. If there are no more current detection scenarios to evaluate, the process may be complete. Alternatively, all current detection scenarios can be identified at one time and some or all may be run substantially simultaneously.

Identification of Voltage-Related EBD Conditions

Figure 6:
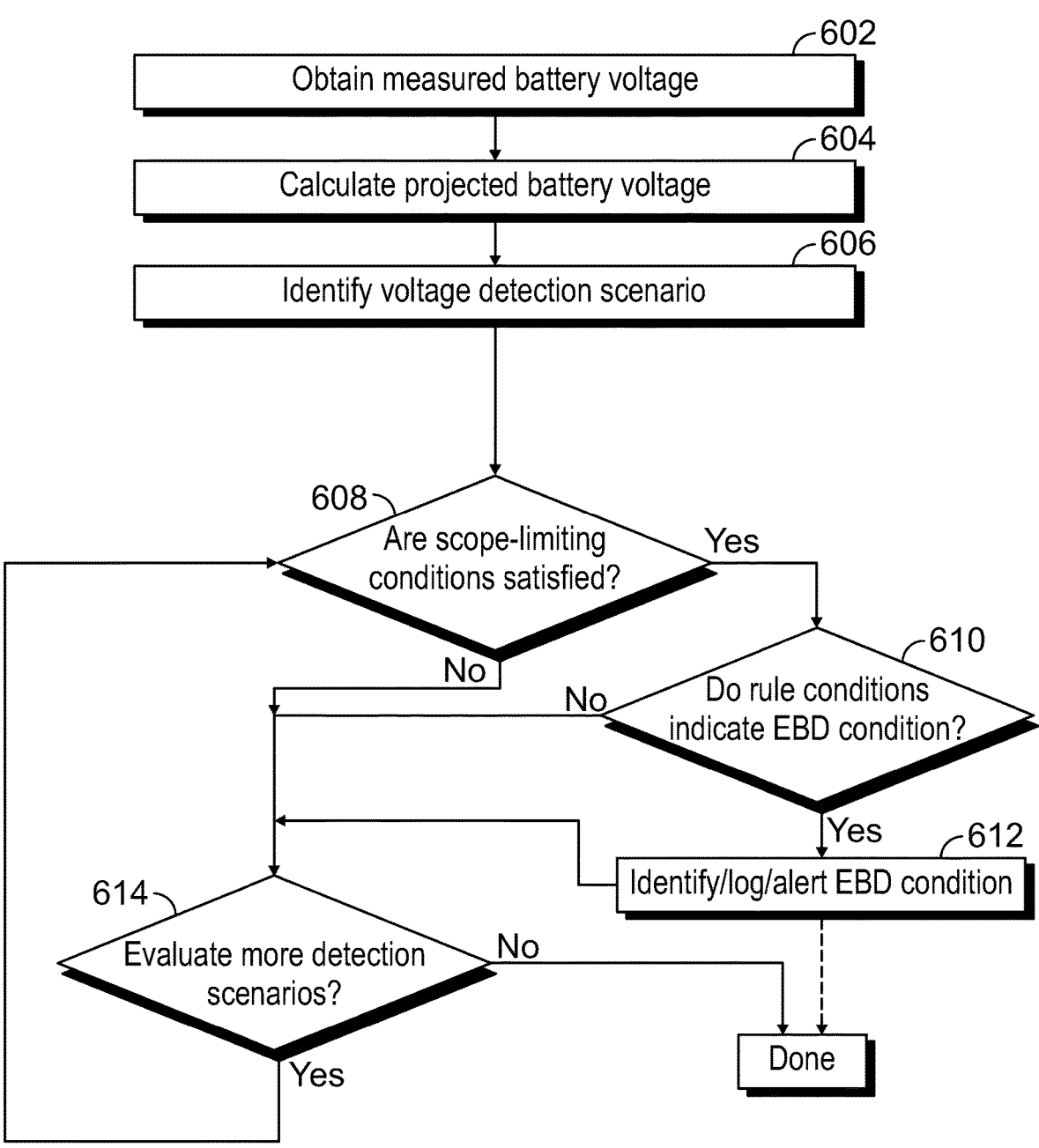
FIG. 6 illustrates a method for evaluating voltage detection scenarios associated with measured and projected battery voltages to identify EBD condition(s) in accordance with embodiments herein.

FIG. 6 illustrates a method for evaluating voltage detection scenarios associated with the measured and projected voltages to identify EBD condition(s) in accordance with embodiments herein. The operations of FIG. 6 may be implemented by hardware, firmware, circuitry and/or one or more processors housed partially and/or entirely within an IMD, a local external device, remote server or more generally within a healthcare system. Optionally, the operations of FIG. 6 may be partially implemented by an IMD and partially implemented by a local external device, remote server or more generally within a healthcare system. For example, the IMD includes IMD memory and one or more IMD processors, while each of the external devices/systems (e.g., local, remote or anywhere within the healthcare system) include external device memory and one or more external device processors.

FIGS. 7A and 7B illustrate a plurality of voltage detection scenarios in accordance with embodiments herein. It should be understood that other voltage detection scenarios can be used with the same, some, or different scope-limiting conditions and rule conditions. The processor(s) evaluate a number of voltage detection scenarios. For example, the processors can be configured to identify one or more faults and/or potential fault conditions, including but not limited to one or more of: i) detecting a large single voltage drop when relaxation is not ongoing, ii) detecting a large single voltage drop when relaxation is ongoing, iii) detecting two medium voltage drops when relaxation is recent, iv) detecting three small voltage drops when relaxation is not ongoing, v)

detecting three small voltage drops when relaxation is recent, vi) a comparison of measured BV to projected BV with a safety margin.

At 602, one or more processors obtain measured BV from over an interrogation period. In some embodiments the battery voltage measurement can be measured and/or obtained on a periodic schedule, such as every day, once within a 12-hour or 24-hour window, and the like, unless suppressed by another factor/setting.

At 604, one or more processors calculate projected BV over a similar measure of time. The measured BV and calculated projected BV can be obtained and/or calculated as discussed above in FIGS. 2A and 2B. For example, referring to FIG. 4A, at approximately day 800 the value of the measured BV 402*a* is approximately 2.98 V and the value of the projected BV 404*a* is approximately 2.915 V.

At 606, one or more processors identify a voltage detection scenario to compare the actual energy usage, reflected in the measured BV 402, to the projected energy usage, reflected in the projected BV 404.

At 608, one or more processors determine whether scope-limiting conditions of the voltage detection scenario are satisfied. With respect to some of the scope-limiting conditions, in some cases the processor may identify the relaxation flag 418, the postponed flag 422, and/or the telemetry flag 424 as shown in FIGS. 4A and 4B. In some embodiments, a scope-limiting condition indicates that one or more values of the measured BV 402 are to be less than a reference value (e.g., approximately 2.8-3 V) to prevent the voltage detection scenario from running early in the life of the IMD.

If all scope-limiting conditions of the voltage detection scenario are satisfied, flow moves to 610 where one or more processors determine whether rule conditions indicate an EBD condition.

Referring to rule 3 of FIG. 7A and to FIG. 1C, if the processors determine that all of the scope-limiting conditions for rule 3 are satisfied at 608, the processor can compare the measured BV pts 120*h*, 120*i*, 120*j*, 120*k* as indicated and calculate differences using the measured BV 102*c* and projected BV 104 points as indicated to determine if, for example, two medium voltage drops have occurred when relaxation is recent. In some embodiments the processors can determine that the decrease in voltage between the measured BV 102*c* and the projected BV 104*c* at days 0, −1, −2, indicate a single large drop according to one of the voltage detection scenarios 1 or 2. In FIG. 1D, in some embodiments the processors can determine that the measured BV 102*d* is less than expected when compared to the projected BV 104*d*, such as by utilizing the voltage detection scenario 6.

Turning to FIG. 4A, an extreme decrease in the measured BV 402*a* occurs around time T1. By way of example only, the voltage detection scenario 1 detects a large single voltage drop when relaxation is NOT ongoing while the voltage detection scenario 2 detects a large single voltage drop when relaxation IS ongoing. In this example, the processors can determine that this decrease in the measured BV 402*a* indicates a possible EBD condition using either the voltage detection scenario 1 or 2.

If the processors determine that the rule conditions indicate an EBD condition, flow passes to 612 where the one or more processors identify and/or log the EBD condition that is indicative of a failure condition that is unrelated to a battery state. In some embodiments, the one or more processors can initiate a warning to notify the patient and/or health care professionals of an EBD condition. In some embodiments the warning can be a communication that is output or transmit to indicate that the device may experience an EBD state. The flow can either continue to 614 or be done.

Returning to 610, if the rule conditions do not indicate an EBD condition, flow passes to 614 where one or more processors determine if there are more voltage detection scenarios to evaluate. For example, if the processors just evaluated the voltage detection scenario 1, the flow may return to 608 and the one or more processors continue to evaluate voltage detection scenarios 2, 3, and so on. If there are no more voltage detection scenarios to evaluate, the process may be done. Alternatively, all of the voltage detection scenarios can be identified at one time and some or all may be run substantially simultaneously.

In the foregoing embodiments, methods and systems are described that identify an EBD condition based on a relationship between projected energy usage and actual energy usage. In some embodiments, an EBD condition is identified when the cell voltage decreases by a predetermined limit/level and/or decreases multiple times within a predetermined period of time. In other embodiments, the EBD condition can also be identified when the measured current deviates from the projected current. Certain limitations can be applied to prevent the false identification of an EBD condition, and to restrict some detection scenarios from being evaluated soon after implantation of the IMD.

Implantable Medical Device

Figure 8:
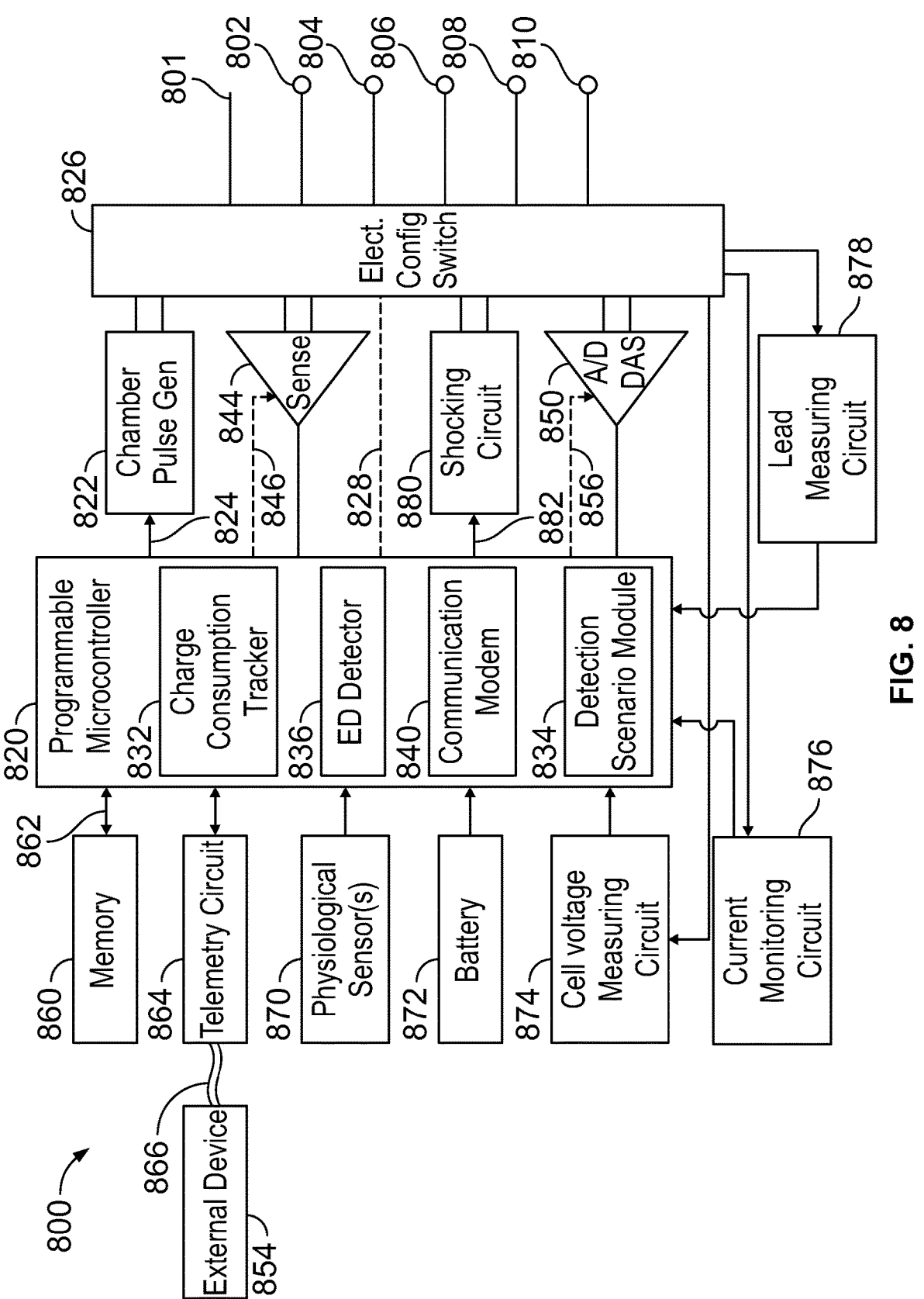
FIG. 8 shows an exemplary IMD that is implanted into the patient as part of the implantable cardiac system in accordance with embodiments herein.

FIG. 8 shows an exemplary IMD 800 that is implanted into the patient as part of the implantable cardiac system. The IMD 800 has a housing 801 to hold the electronic/computing components. The housing 801 (which is often referred to as the "can", "case", "encasing", or "case electrode") may be programmably selected to act as the return electrode for certain stimulus modes. Housing 801 further includes a connector (not shown) with a plurality of terminals 802, 804, 806, 808, and 810. The terminals may be connected to electrodes that are located directly on the housing of the IMD 800 and/or connected to one or more leads that are located at various locations within and about the heart. The type and location of each electrode may vary. The IMD 800 includes a programmable microcontroller 820 that controls various operations of the IMD 800, including cardiac monitoring and stimulation therapy, and is configured to execute program instructions. Microcontroller 820 includes a microprocessor (or equivalent control circuitry), RAM and/or ROM memory, logic and timing circuitry, state machine circuitry, and I/O circuitry.

The IMD 800 includes a cell voltage measuring circuit 874 configured to measure the voltage across the battery cell as explained herein. For example, the cell voltage measuring circuit 874 can measure cell voltage at a point in time. The IMD 800 also includes a current monitoring circuit 876 configured to measure the current drawn during steady state and during one or more tasks as explained herein. The cell voltage measuring circuit 874 and/or the current monitoring circuit 876 can therefore measure an actual energy usage from the battery that represents at least one of a current draw from the battery during the corresponding tasks and steady state, or a voltage measurement across the battery.

The microcontroller 820 includes a charge consumption tracker 832, an early depletion detector 836, a detection scenario module 834, and other logic to perform the methods described herein. The charge consumption tracker 832 accesses values measured by the cell voltage measuring circuit 874 and the current monitoring circuit 876. The charge consumption tracker 832 tracks steady state and device related tasks performed by the IMD 800 and based thereon determines a steady state charge consumption life to date for the medical device and task related charge consumption life to date for the medical device. The charge consumption tracker 832 performs the various charge consumption related operations described throughout. For example, the charge consumption tracker 832 calculates a projected energy usage from the battery in connection with the corresponding tasks based on programmed device parameters and/or measurements.

In some embodiments, the current monitoring circuit 876 in connection with measuring the actual energy usage associated with a first task within one or more tasks, is configured to obtain current measurement values of current drawn from the battery while the circuitry and the processor perform the first task, and the charge consumption tracker 832 combines the current measurement values to obtain the actual energy usage associated with the first task. In some embodiments, the current monitoring circuit 876 obtains current measurements and the charge consumption tracker 832 combines the current measurement values across multiple tasks within the one or more tasks. In other embodiments, the actual energy usage includes a current drawn actually from the battery while performing a corresponding task, and the projected energy usage includes a projected current expected to be drawn from the battery while performing the corresponding task.

In some embodiments, the microcontroller 820 calculates projected energy usage from the battery in connection with one or more corresponding tasks. In other embodiments, the calculation of the projected energy usage from the battery in connection with the corresponding tasks is based in part on programmed device parameters stored in the memory. In some embodiments, measurements, such as lead resistance, can also be included when the projected energy usage is calculated. For example, a lead measuring circuit 878 can measure resistance of one or more of the leads connected with the terminals 802, 804, 806, 808, and 810. The lead resistance can be used to calculate a projected energy usage. The microcontroller 820 also calculates projected BV and measured average current based on measured charge consumption.

The early depletion detector 836 declares an EBD condition based on a relation between projected energy usage and actual energy usage. In some embodiments the EBD condition is indicative of a failure condition that is unrelated to a battery state. In other cases, the EBD condition is indicative of a failure condition that is related to a failure in at least one of circuitry, a processor, a lead, hermeticity seal break, or malfunctioning software or firmware.

An EBD condition can be indicated by unexpected behavior of the battery voltage or current, such as a sudden unscheduled voltage drop not due to normal operation, one or more voltage drops within a predetermined amount of time, and/or an unexpected increase in measured average current. For example, the early depletion detector 836 declares an EBD condition based on a relation between measured average current and projected current. The early depletion detector 836 also compares the measured and projected cell voltages to determine whether the difference there-between falls within a tolerance range. Based on the relation between the measured and projected cell voltages, projected and actual energy usage, and/or the measured and projected currents, the early depletion detector 836 declares an early depletion condition and initiates a warning operation.

The detection scenario module 834 evaluates current detection scenarios and voltage detection scenarios to determine relationships between actual energy usage and projected energy usage. The detection scenario module 834 determines whether scope-limiting conditions for applicable current and/or voltage detection scenarios are satisfied and determines whether rule condition(s) indicate an EBD condition.

In some embodiments, the detection scenario module 834 compares the actual energy usage to the projected energy usage and evaluates a collection of scope-limiting conditions related to the current detection scenario. In some embodiments, the projected energy usage is combined with a tolerance and the EBD condition is identified when the actual energy usage is greater than the projected energy usage with the tolerance. In other embodiments, the collection of scope-limiting conditions includes evaluating a predetermined number of points within an interrogation period that are uninterrupted in time by a telemetry session.

In yet further embodiments, the detection scenario module 834 determines the EBD condition by identifying a voltage detection scenario that compares a plurality of the voltage measurements within an interrogation period, and evaluates a collection of scope-limiting conditions related to the voltage detection scenario. In some embodiments, the collection of scope-limiting conditions includes at least one of i) determining whether at least one of the voltage measurements is in relaxation, ii) determining whether at least one of the voltage measurements is greater than a predetermined voltage value, iii) determining whether at least one of the voltage measurements is a postponed measurement, or iv) determining whether at least one of the voltage measurements is newer than a most recent telemetry session. The determination of the EBD condition can further include evaluating a collection of rule conditions that include at least one of i) determining that one or more voltage drop of the voltage measurements exceeds predetermined limits, or ii) that at least one of the voltage measurements is below a projected voltage level combined with a safety margin.

In some embodiments, the detection scenario module 834 determines the EBD condition by identifying a first current or voltage detection scenario that includes a collection of scope-limiting conditions and compares the actual energy usage to the projected energy usage. In response to satisfying the collection of scope-limiting conditions, the detection scenario module 834 evaluates a collection of rule conditions related to the first detection scenario, and in response to determining that the EBD condition is not occurring, identifies a second detection scenario to determine the EBD condition.

The IMD 800 further includes a pulse generator 822 that generates stimulation pulses for delivery by one or more electrodes coupled thereto. The pulse generator 822 is controlled by the microcontroller 820 via control signal 824. The pulse generator 822 is coupled to the select electrode(s) via an electrode configuration switch 826, which includes multiple switches for connecting the desired electrodes to the appropriate I/O circuits, thereby facilitating electrode programmability. The switch 826 is controlled by a control signal 828 from the microcontroller 820. In the example of FIG. 8, a single pulse generator 822 is illustrated. Optionally, the IMD 800 may include multiple pulse generators, similar to pulse generator 822, where each pulse generator is coupled to one or more electrodes and controlled by the microcontroller 820 to deliver select stimulus pulse(s) to the corresponding one or more electrodes.

Microcontroller 820 includes various modules to implement the functionality of the IMD 800. For example, the microcontroller 820 controls the timing of the stimulation pulses (e.g., pacing rate, atrio-ventricular (AV) delay, atrial interconduction (A-A) delay, or ventricular interconduction (V-V) delay, etc.). Microcontroller 820 detects arrhythmia conditions and may review and analyze one or more features of the morphology of cardiac signals. Although not shown, the microcontroller 820 may further include other dedicated circuitry and/or firmware/software components that assist in monitoring various conditions of the patient's heart and managing pacing therapies.

The IMD 800 is further equipped with a communication modem (modulator/demodulator) 840 to enable wireless communication with other devices, implanted devices and/or external devices. In one implementation, the communication modem 840 may use high frequency modulation of a signal transmitted between a pair of electrodes. As one example, the signals may be transmitted in a high frequency range as such signals travel through the body tissue and fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller as a standalone component.

The IMD 800 includes sensing circuitry 844 selectively coupled to one or more electrodes that perform sensing operations, through the switch 826 to detect the presence of cardiac activity in the right chambers of the heart. The sensing circuitry 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the IMD 800 to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of the sensing circuitry 844 is connected to the microcontroller 820 which, in turn, triggers or inhibits the pulse generator 822 in response to the absence or presence of cardiac activity. The sensing circuitry 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

In the example of FIG. 8, a single sensing circuit 844 is illustrated. Optionally, the IMD 800 may include multiple sensing circuits, similar to sensing circuit 844, where each sensing circuit is coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The IMD 800 further includes an analog-to-digital (A/D) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters (e.g., programmed device parameters, program instructions) used by the microcontroller 820 are stored in memory 860 and used to customize the operation of the IMD 800 to suit the needs of a particular patient. The operating parameters of the IMD 800 may be non-invasively programmed into the memory 860 through a telemetry circuit 864 in telemetric communication via communication link 866 with the external device 854. For example, programmed device parameters can be received from the external device 854 and updated as needed. In some embodiments, programmed device parameters can include pacing current usage by various leads attached to the device, pacing rate, pacing pulse width, pacing pulse shape, pacing voltage, and/or percent chamber pacing.

The telemetry circuit 864 allows intracardiac electrograms and status information relating to the operation of the IMD 800 (as contained in the microcontroller 820 or memory 860) to be sent to the external device 854 through the established communication link 866.

The IMD 800 can further include one or more physiologic sensors 870. Such sensors are commonly referred to as "rate-responsive" sensors because they are typically used to adjust pacing stimulation rates according to the exercise state of the patient. The one or more physiologic sensors 870 collect signals indicative of physiologic activity that can be analyzed, such as by the microcontroller 820.

A battery 872 provides operating power to all of the components in the IMD 800, such as to supply energy in connection with performing one or more tasks. The battery 872 is capable of operating at low current drains for long periods of time, and is capable of providing high-current pulses (for capacitor charging) when the patient requires a shock pulse (e.g., in excess of 2 A, at voltages above 2 V, for periods of 120 seconds or more). The battery 872 also desirably has a predictable discharge characteristic so that elective replacement time can be detected. As one example, the IMD 800 employs lithium/silver vanadium oxide batteries.

The IMD 800 may be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 820 further controls a shocking circuit 880 by way of a control signal 882. The shocking circuit 880 generates shocking pulses of low (e.g., up to 0.5 joules), moderate (e.g., 0.5-10 joules), or high energy (e.g., 11 to 40 joules), as controlled by the microcontroller 820. Such shocking pulses are applied to the patient's heart through shocking electrodes to deliver a therapy. It is noted that the shocking circuit 880 is optional and may not be implemented in the IMD, as the various slave pacing units described below will typically not be configured to deliver high voltage shock pulses.

External Device

Figure 9:
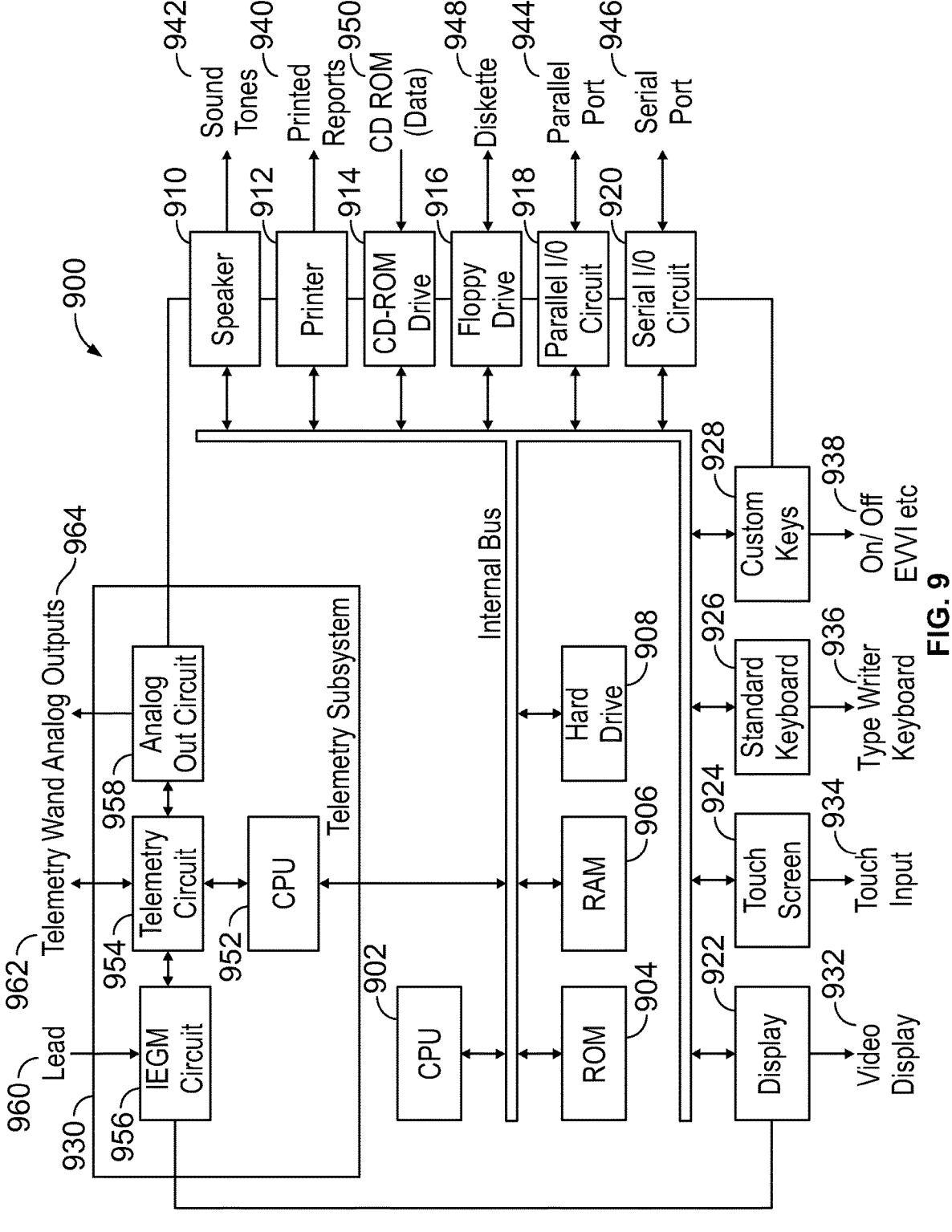
FIG. 9 illustrates a functional block diagram of the external device that is operated in accordance with embodiments herein.

FIG. 9 illustrates a functional block diagram of the external device 900 that is operated in accordance with the processes described herein and to interface with implantable medical devices as described herein. The external device 900 may be a workstation, a portable computer, an IMD programmer, a PDA, a cell phone and the like. The external device 900 includes an internal bus that connects/interfaces with a Central Processing Unit (CPU) 902, ROM 904, RAM 906, a hard drive 908, the speaker 910, a printer 912, a CD-ROM drive 914, a floppy drive 916, a parallel I/O circuit 918, a serial I/O circuit 920, the display 922, a touch screen 924, a standard keyboard connection 926, custom keys 928, and a telemetry subsystem 930. The internal bus is an address/data bus that transfers information between the various components described herein. The hard drive 908 may store operational programs as well as data, such as waveform templates and detection thresholds.

The CPU 902 typically includes a microprocessor, a micro-controller, or equivalent control circuitry, designed specifically to control interfacing with the external device 900 and with the IMD. The CPU 902 performs the processes discussed above. For example, the CPU 902 may perform all or a portion of the determinations of steady state charge consumption, task related charge consumption, total charge consumption, as well as the determination of whether measured in projected cell voltages fall within tolerance ranges of one another. The CPU 902 may perform the calibration operations described herein, as well as the various methods for determining whether early completion conditions exist and initiating warnings.

The CPU 902 may include RAM or ROM memory, logic and timing circuitry, state machine circuitry, and I/O circuitry to interface with the IMD. The display 922 (e.g., may be connected to the video display 932). The touch screen 924 may display graphic information relating to the IMD. The display 922 displays various information related to the processes described herein. The touch screen 924 accepts a user's touch input 934 when selections are made. The keyboard 926 (e.g., a typewriter keyboard 936) allows the user to enter data to the displayed fields, as well as interface with the telemetry subsystem 930. Furthermore, custom keys 928 turn on/off 938 (e.g., EVVI) the external device 900. The printer 912 prints copies of reports 940 for a physician to review or to be placed in a patient file, and speaker 910 provides an audible warning (e.g., sounds and tones 942) to the user. The parallel I/O circuit 918 interfaces with a parallel port 944. The serial I/O circuit 920 interfaces with a serial port 946. The floppy drive 916 accepts diskettes 948. Optionally, the floppy drive 916 may include a USB port or other interface capable of communicating with a USB device such as a memory stick. The CD-ROM drive 914 accepts CD ROMs 950.

The telemetry subsystem 930 includes a central processing unit (CPU) 952 in electrical communication with a telemetry circuit 954, which communicates with both an IEGM circuit 956 and an analog out circuit 958. The circuit 956 may be connected to leads 960. The circuit 956 is also connected to the implantable leads to receive and process IEGM cardiac signals as discussed above. Optionally, the IEGM cardiac signals sensed by the leads may be collected by the IMD and then transmitted, to the external device 900, wirelessly to the telemetry subsystem 930 input.

The telemetry circuit 954 is connected to a telemetry wand 962. The analog out circuit 958 includes communication circuits to communicate with analog outputs 964. The external device 900 may wirelessly communicate with the IMD and utilize protocols, such as Bluetooth, GSM, infrared wireless LANs, HIPERLAN, 3G, satellite, as well as circuit and packet data protocols, and the like. Alternatively, a hard-wired connection may be used to connect the external device 900 to the IMD.

Alternative Embodiments

Embodiments may be implemented in connection with one or more implantable medical devices (IMDs). Nonlimiting examples of IMDs include one or more of neuro-stimulator devices, implantable leadless monitoring and/or therapy devices, left ventricular assist devices, percutaneous heart pump devices, implantable heart assist devices, and/or alternative implantable medical devices. For example, the IMD may represent a cardiac monitoring device, pacemaker, cardioverter, cardiac rhythm management device, defibril-lator, neurostimulator, leadless monitoring device, leadless pacemaker and the like. For example, the IMD may include one or more structural and/or functional aspects of the device(s) described in U.S. Pat. No. 9,333,351 "Neurostimu-lation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may be a leadless implantable medical device (LIMD) that include one or more structural and/or functional aspects of the device(s) described in U.S. Pat. No. 9,216,285 "Lead-less Implantable Medical Device Having Removable And Fixed Components" and U.S. Pat. No. 8,831,747 "Leadless Neurostimulation Device And Method Including The Same", which are hereby incorporated by reference. Addi-tionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implant-able Medical Device", which are hereby incorporated by reference. Additionally or alternatively, the IMD may be a subcutaneous IMD that includes one or more structural and/or functional aspects of the device(s) described in U.S. Pat. No. 10,765,860, titled "Subcutaneous Implantation Medical Device With Multiple Parasternal-Anterior Elec-trodes"; U.S. Pat. No. 10,722,704, titled "Implantable Medi-cal Systems And Methods Including Pulse Generators And Leads"; U.S. Pat. No. 11,045,643, titled "Single Site Implan-tation Methods For Medical Devices Having Multiple Leads", which are hereby incorporated by reference in their entireties. Additionally or alternatively, the IMD may include one or more structural and/or functional aspects of the device(s) described in U.S. Pat. No. 9,138,518 "Percu-taneous Heart Pump" and U.S. Pat. No. 7,331,921 "Implant-able Heart Assist System", which are hereby incorporated by reference. Additionally or alternatively, embodiments herein may be implemented in combination with the processes and structures described in U.S. Pat. No. 11,221,373, titled "Method and Device for Detecting Early Battery Depletion Condition", issuing Jan. 11, 2022. Additionally or alterna-tively, embodiments herein may be implemented in combi-nation with the processes and structures described in U.S. Pat. No. 11,211,805, titled "Methods, Systems, And Devices that Estimate Longevity Of An Implantable Medical Device", issuing Dec. 28, 2021. Further, one or more com-binations of IMDs may be utilized from the above incorpo-rated patents and applications in accordance with embodi-ments herein.

All references, including publications, patent applications and patents, cited herein are hereby incorporated by refer-ence to the same extent as if each reference were individu-ally and specifically indicated to be incorporated by refer-ence and were set forth in its entirety herein.

CLOSING

It should be clearly understood that the various arrange-ments and processes broadly described and illustrated with respect to the Figures, and/or one or more individual com-ponents or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more com-puter (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, elec-tromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network inter-face via a network to a second device having a second processor for execution of the code on the second device.

Aspects are described herein with reference to the Fig-ures, which illustrate example methods, devices and pro-gram products according to various example embodiments. These program instructions may be provided to a processor of a general purpose computer, special purpose computer, or other programmable data processing device or information handling device to produce a machine, such that the instruc-tions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage elements may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device (IMD), comprising:
memory configured to store program instructions;
a processor configured to execute the program instructions;
circuitry electrically coupled to the processor, the circuitry and processor configured to perform one or more tasks in connection with at least one of i) collecting signals indicative of physiologic activity, ii) analyzing the signals collected, iii) delivering a therapy, or iv) communicating with an external device;
a battery configured to supply energy to the circuitry and the processor in connection with performing the one or more tasks; and
a monitoring circuit coupled to the battery, the monitoring circuit configured to measure an actual energy usage from the battery, the actual energy usage representing at least one of a current draw from the battery during the corresponding tasks within an interrogation period or a voltage measurement across the battery within the interrogation period;
wherein the circuitry and processor are further configured to determine when an early battery depletion (EBD) condition exists based on a relationship between a projected energy usage from the battery and the actual energy usage compared within at least a portion of the interrogation period.

2. The IMD of claim 1, wherein the EBD condition is indicative of a failure condition that is unrelated to a battery state and wherein the projected energy usage from the battery in connection with the corresponding tasks is based in part on programmed device parameters.

3. The IMD of claim 1, wherein the determination of the EBD condition includes comparing two or more points in time within the interrogation period to detect one or more deviations between the projected energy usage and the actual energy usage.

4. The IMD of claim 3, wherein the actual energy usage is a measured average current.

5. The IMD of claim 3, wherein the one or more deviations are compared to predetermined rule conditions, the rule conditions being based in part on the number of the two or more points in time following a telemetry session.

6. The IMD of claim 1, wherein the circuitry and processor are further configured to determine that a telemetry session occurred within the interrogation period, the determination of the EBD condition including determining the relationship between the projected energy usage and the actual energy usage within the interrogation period with respect to the telemetry session.

7. The IMD of claim 1, wherein, in connection with measuring the actual energy usage associated with a first task within the one or more tasks, the monitoring circuitry is configured to:
obtain current measurement values of current drawn from the battery while the circuitry and the processor perform the first task; and
combine the current measurement values to obtain the actual energy usage associated with the first task.

8. The IMD of claim 1, wherein the actual energy usage includes a current drawn actually from the battery while performing a corresponding task, and the projected energy usage includes a projected current expected to be drawn from the battery while performing a corresponding task.

9. The IMD of claim 1, wherein the determination of the EBD condition includes:

identifying a voltage detection scenario that compares a plurality of the voltage measurements within the interrogation period; and evaluating a collection of scope-limiting conditions related to the voltage detection scenario.

10. The IMD of claim 9, wherein the collection of scope-limiting conditions includes evaluating a number of points within a period of time that is less than the interrogation period.

11. The IMD of claim 9, wherein the collection of scope-limiting conditions includes at least one of i) determining whether at least one of the voltage measurements is in relaxation, ii) determining whether at least one of the voltage measurements is greater than a predetermined voltage value, iii) determining whether at least one of the voltage measurements is a postponed measurement, or iv) determining whether at least one of the voltage measurements is newer than a most recent telemetry session, and wherein the determination of the EBD condition further includes evaluating a collection of rule conditions that include at least one of i) determining one or more voltage drop of the voltage measurements that exceeds predetermined limits, or ii) at least one of the voltage measurements is below a projected voltage level combined with a safety margin.

12. The IMD of claim 1, wherein the circuitry and the processor are further configured to, in response to determining that the EBD condition exists, communicate a warning to the external device or initiate a warning indicator.

13. The IMD of claim 1, wherein the determination of the EBD condition includes:

identifying a first detection scenario that compares the actual energy usage to the projected energy usage, wherein the first detection scenario is a current detection scenario or a voltage detection scenario, wherein the first detection scenario includes a collection of scope-limiting conditions;

in response to satisfying the collection of scope-limiting conditions, evaluating a collection of rule conditions related to the first detection scenario; and in response to the collection of rule conditions indicating that the EBD condition is not occurring, identifying a second detection scenario to determine the EBD condition.

14. A computer implemented method, comprising:

under control of one or more processors, configured with specific executable instructions, utilizing a battery to supply energy to circuitry and the one or more processors in connection with performing tasks in connection with at least one of i) collecting signals indicative of physiologic activity, ii) analyzing the signals collected, iii) delivering a therapy, or iv) communicating with an external device;

directing a monitoring circuit to measure an actual energy usage from the battery, the actual energy usage representing at least one of a current draw from the battery during the corresponding tasks within an interrogation period or a voltage measurement across the battery within the interrogation period; and determining when an early battery depletion (EBD) condition exists based on a relationship between a projected energy usage from the battery and the actual energy usage compared within at least a portion of the interrogation period.

15. The method of claim 14, further comprising:

receiving programmed device parameters; and storing the programmed device parameters in a memory, the determining the EBD condition based on the actual energy usage occurring after the programmed device parameters are received, wherein the projected energy usage from the battery in connection with the corresponding tasks is based in part on the programmed device parameters.

16. The method of claim 14, wherein the determining of the EBD condition includes comparing two or more points in time within the interrogation period to detect one or more deviations between the projected energy usage and the actual energy usage.

17. The method of claim 16, wherein the actual energy usage is a measured average current.

18. The method of claim 16, further comprising comparing the one or more deviations to predetermined rule conditions, the rule conditions being based in part on a number of the two or more points in time following a telemetry session.

19. The method of claim 14, further comprising determining that a telemetry session occurred within the interrogation period, the determination of the EBD condition including determining the relationship between the projected energy usage and the actual energy usage within the interrogation period with respect to the telemetry session.

20. The method of claim 14, further comprising, in response the determining that the EBD condition exists, communicating a warning to the external device or initiating a warning indicator.

* * * * *